US007049134B2

(12) United States Patent
Palmer et al.

(10) Patent No.: US 7,049,134 B2
(45) Date of Patent: May 23, 2006

(54) ROLLING CIRCLE REPLICON EXPRESSION VECTOR

(75) Inventors: Kenneth E. Palmer, Vacaville, CA (US); Gregory P. Pogue, Vacaville, CA (US)

(73) Assignee: Large Scale Biology Corporation, Vacaville, CA (US)

( * ) Notice: Subject to any disclaimer, the term of this patent is extended or adjusted under 35 U.S.C. 154(b) by 351 days.

(21) Appl. No.: 10/286,186

(22) Filed: Nov. 1, 2002

(65) Prior Publication Data

US 2003/0143741 A1 Jul. 31, 2003

Related U.S. Application Data

(63) Continuation of application No. 09/505,477, filed on Feb. 16, 2000, now abandoned.

(51) Int. Cl.
*C12N 15/79* (2006.01)
*C12N 15/82* (2006.01)
*C12N 15/85* (2006.01)
*C12N 7/00* (2006.01)
*A61K 31/713* (2006.01)

(52) U.S. Cl. ............... 435/320.1; 435/455; 435/235.1; 514/44

(58) Field of Classification Search ............... 435/456, 435/320.1, 235.1, 455; 514/44
See application file for complete search history.

(56) References Cited

U.S. PATENT DOCUMENTS 6,287,856 B1 9/2001 Poet et al.

FOREIGN PATENT DOCUMENTS

WO WO 99/29871 6/1999
WO WO 99/49079 9/1999
WO WO 99/60140 11/1999

OTHER PUBLICATIONS

Needham, P.D. et al., "GUS expression patterns from a tobacco yellow dwarf virus-based episomal vector", 1998, Plant Cell Reports, vol. 17: p. 631-639.*
Xie, Q. et al. "Plant cells contain a novel member of the retinoblastoma family of growth regulatory proteins", 1995, EMBO Journal, vol. 15: p. 4900-4908.*
Xie, Q. et al. "Identification and analysis of a retinoblastoma binding motif in the replication protein of a plant DNA virus: requirement for efficient viral DNA replication", 1995, EMBO J., vol. 14: p. 4073-4082.*
Castellano, M., et al., "Initiation of DNA Replication in a Eukaryotic Rolling-circle Replicon: Identification of Multiple DNA-protein Complexes at the Geminivirus Origin," *JMB* Aticle No. 2916 (1999).

Gibbs, M., et al., "Evidence that a plant virus switched hosts to infect a vertebrate and then recombined with a vertebrate-infecting virus," *Proc. Natl. Acad. Sci. USA* 96:8022-8027 (1999).
Harnel, A., et al., "Nucleotide Sequence of Porcine Circovirus Associated with Postweaning Multisystemic Wasting Syndrome in Pigs," *J. Virology* 72(6):5262-5267 (1998).
Hanley-Bowdoin, L., et al., "Geminiviruses: Models for Plant DNA Replication, Transcription, and Cell Cycle Regulation," *Critical Reviews in Plant Sciences!18*(1):71-106 (1999).
Mankertz, A., et al., "Identification of a protein essential for replication of porcine circovirus," *J. Gen. Virol.* 79:381-384 (1998).
Mankertz, A., et al., "Mapping and Characterization of the Origin of DNA Replication of Porcine Circovirus," *J. Virology* 71(3):2562-2566.
Mankertz, J., et al., "Transcription Analysis of Porcine Circovirus (PCV)," *Virus Genes* 163:267-276 (1998).
Meehan, B., et al., "Characterization of novel circovirus DNAs associated with wasting syndromes in pigs," *J. Gen. Virol.* 79:2171-2179 (1998).
Meehan, B., et al., "Sequence of porcine circovirus DNA: affinities with plant circoviruses," *J. Gen. Virol.* 78:221-227 (1997).
Mushahwar, I., et al., "Molecular and biophysical characterization of TT virus: Evidence for a new virus family infecting humans," *Proc. Natl. Acad. Sci. USA* 96:3177-3182 (1999).
Orozco, B., et al., "Functional Domains of a Geminivirus Replication Protein," *J. Biological Chemistry* 272(15):9840-9846 (1997).

(Continued)

*Primary Examiner*—David Guzo
*Assistant Examiner*—Michael D. Burkhart
(74) *Attorney, Agent, or Firm*—Paul Littlepage; Thomas Gallegos; Quine Intellectual Property Law Group, P.C.

(57) ABSTRACT

A rolling circle DNA replicon which replicates in a host eukaryotic cell is disclosed which has a truncated replication cycle. The rolling circle DNA replicon comprises the following elements present on the same DNA molecule. It contains a Rep gene open reading frame from a virus belonging to the viral taxonomic families Geminiviridae, Circoviridae or genus Nanovirus. The Rep gene open reading frame is placed under transcriptional control of a promoter, which is placed 5' of the gene. Any sequences that are required to be present in cis on the rolling circle DNA replicon in order that the Rep protein might promote replication of the rolling circle DNA replicon are included. An expression cassette for expression of an ancillary protein that is capable of creating a cellular environment permissive for replication of the rolling circle DNA replicon in the host cell of interest is also included. At least one expression cassette with an RNA polymerase II promoter, a multiple cloning site, and transcription termination and polyadenylation signals suitable for transcription of RNA molecules not normally intrinsic to a geminiviral, circoviral or nanoviral genome is also included.

13 Claims, 8 Drawing Sheets

OTHER PUBLICATIONS

Palmer, K. and Rybicki, E., The Molecular Biology of Mastreviruses, *Advances in Virus Reserach 50*:183-234 (1998).

Palmer, K. and Rybicki, E., The use of geminiviruses in biotechnology and plant molecular biology, with particular focus on Mastreviruses, *Elsevier Plant Science 129*:115-130 (1997).

Palmer, K., et al., "Generation of maize cell lines contaiing autonomously replicating maize streak virus-based gene vectors," *Arch. Virol. 144*:1345-1360 (1999).

Timmermans, M., et al., "Geminiviruses and Their Uses as Extrachromosomal Replicons," *Annu. Rev. Plant Physiol Plant Mol. Biol. 45*:79-112 (1994).

Fire, et al., "Rolling replication of short DNA circles", *Proceedings of the National Academy of Sciences of USA, National Academy of Science, 92*(10):4641-4645 (1995).

Lewin, "Replication Can Proceed Through Eyes, Rolling Circles, or D Loops," *Genes*, 4 Oxford, Oup, GB, 336-338 (1990).

Saunders, et al. "DNA Forms of the Geminivirus African Cassava Mosaic Virus Consistent with a Rolling circle Mechanism of Replication," *Nucleic Acids Research 19*(9):2325-2330 (1991).

Noteborn, et al., "Chicken Anemia Virus Strains with a Mutated Enhancer/Promoter Region Share Reduced Virus Spread and Cytopathogenicity", Elsevier Science B.V., 223:12, pp. 165-172 (1988).

* cited by examiner

FIGURE 1: Restriction and genetic map of Construct 1

FIGURE 2: Restriction and genetic map of Construct 2

FIGURE 3: Restriction and Genetic Map of Construct 6 (pTracerSV40 from Invitrogen Corp)

FIGURE 5
Construct 1 sequence: 5285 bp
Composition   1216 A;  1277 C;  1514 G;  1278 T;  0 OTHER
Percentage:   23%  A;  24%  C;  29%  G;  24%  T;  0%OTHER
Molecular Weight (kDa): ssDNA: 1636.28   dsDNA: 3258.4

ORIGIN
```
1     AGCGCCCAAT ACGCAAACCG CCTCTCCCCG CGCGTTGGCC GATTCATTAA TGCAGCTGGC
61    ACGACAGGTT TCCCGACTGG AAAGCGGGCA GTGAGCGCAA CGCAATTAAT GTGAGTTAGC
121   TCACTCATTA GGCACCCCAG GCTTTACACT TTATGCTTCC GGCTCGTATG TTGTGTGGAA
181   TTGTGAGCGG ATAACAATTT CACACAGGAA ACAGCTATGA CCATGATTAC GCCAAGCTAT
241   TTAGGTGACA CTATAGAATA CTCAAGCTAT GCATCAAGCT TGGTACCGAG CTCGGATCCA
301   CTAGTAACGG CCGCCAGTGT GCTGGAATTC GCCCTTATTT AAATGGAGCC ACAGCTGGTT
361   TCTTTTATTA TTTGGGTGGA ACCAATCAAT TGTTTGGTCC AGCTCAGGTT TGGGGGTGAA
421   GTACCTGGAG TGGTAGGTAA AGGGCTGCCT TATGGTGTGG CGGGAGGAGT AGTTAATATA
481   GGGGTCATAG GCCAAGTTGG TGGAGGGGGT TACAAAGTTG GCATCCAAGA TAACAACAGT
541   GGACCCAACA CCTCTTTGAT TAGAGGTGAT GGGGTCTCTG GGTAAAATT CATATTTAGC
601   CTTTCTAATA CGGTAGTATT GGAAAGGTAG GGGTAGGGGG TTGGTGCCGC CTGAGGGGGG
661   GAGGAACTGG CCGATGTTGA ATTTGAGGTA GTTAACATTC CAAGATGGCT GCGAGTATCC
721   TCCTTTTATG GTGAGTACAA ATTCTGTAGA AAGGCGGGAA TTGAAGATAC CGTCTTTCG
781   GCGCCATCTG TAACGGTTTC TGAAGGCGGG GTGTGCCAAA TATGGTCTTC TCCGGAGGAT
841   GTTTCCAAGA TGGCTGCGGG GGCGGGTCCT TCTTCTGCGG TAACGCCTCC TTGGCCACGT
901   CATCCTATAA AAGTGAAAGA AGTGCGCTGC TGTAGTATTA CCAGCGCACT TCGGCAGCGG
961   CAGCACCTCG GCAGCGTCAG TGAAAATGCC AAGCAAGAA AGCGGCCCGC AACCCCATAA
1021  GAGGTGGGTG TTCACCCTTA ATAATCCTTC CGAGGAGGAG AAAAACAAAA TACGGGAGCT
1081  TCCAATCTCC CTTTTTGATT ATTTTGTTTG CGGAGAGGAA GGTTTGGAAG AGGGTAGAAC
1141  TCCTCACCTC CAGGGGTTTG CGAATTTTGC TAAGAAGCAG ACTTTTAACA AGGTGAAGTG
1201  GTATTTTGGT GCCCGCTGCC ACATCGAGAA AGCGAAAGGA ACCGACCAGC AGAATAAAGA
1261  ATACTGCAGT AAAGAAGGCC ACATACTTAT CGAGTGTGGA GCTCCGCGGA ACCAGGGGAA
1321  GCGCAGCGAC CTGTCTACTG CTGTGAGTAC CCTTTTGGAG ACGGGTCTT TGGTGACTGT
1381  AGCCGAGCAG TTCCCTGTAA CGTATGTGAG AAATTCCGC GGGCTGGCTG AACTTTGAA
1441  AGTGAGCGGG AAGATGCAGC AGCGTGATTG GAAGACAGCT GTACACGTCA TAGTGGGCCC
1501  GCCCGGTTGT GGGAAGAGCC AGTGGGCCCG TAATTTTGCT GAGCCTAGGG ACACCTACTG
1561  GAAGCCTAGT AGAAATAAGT GGTGGGATGG ATATCATGGA GAAGAAGTTG TTGTTTTGGA
1621  TGATTTTTAT GGCTGGTTAC CTTGGGATGA TCTACTGAGA CTGTGTGACC GGTATCCATT
1681  GACTGTAGAG ACTAAAGGGG GTACTGTTCC TTTTTTGGCC CGCAGTATTT TGATTACCAG
1741  CAATCAGGCC CCCCAGGAAT GGTACTCCTC AACTGCTGTC CCAGCTGTAG AAGCTCTCTA
1801  TCGGAGGATT ACTACTTTGC AATTTTGGAA GACTGCTGGA GAACAATCCA CGGAGGTACC
1861  CGAAGGCCGA TTTGAAGCAG TGGACCCACC CTGTGCCCTT TTCCCATATA AAATAAATTA
1921  CTGAGTCTTT TTTGTTATCA CATCGTAATG GTTTTTATTT TTATTTATTT AGAGGGTCTT
1981  TTAGGATAAA TTCTCTGAAT TGTACATAAA TAGTCAGCCT ACCACATAA TTTTGGGCTG
2041  TGGCTGCATT TTGGAGCGCA TAGCCGAGGC CTGTGTGCTC GACATTGGTG TGGGTATTTA
2101  AAAAGGGCGA ATTCTGCAGA TATCCATCAC ACTGGCGGCC GCTCGAGCAT GCATCTAGAG
2161  GGCCCAATTC GCCCTATAGT GAGTCGTATT ACAATTCACT GGCCGTCGTT TTACAACGTC
2221  GTGACTGGGA AAACCCTGGC GTTACCCAAC TTAATCGCCT TGCAGCACAT CCCCCTTTCG
2281  CCAGCTGGCG TAATAGCGAA GAGGCCCGCA CCGATCGCCC TTCCCAACAG TTGCGCAGCC
2341  TATACGTACG GCAGTTTAAG GTTTACACCT ATAAAGAGA GAGCCGTTAT CGTCTGTTTG
2401  TGGATGTACA GAGTGATATT ATTGACACGC CGGGGCGACG GATGGTGATC CCCCTGGCCA
2461  GTGCACGTCT GCTGTCAGAT AAAGTCTCCC GTGAACTTTA CCCGGTGGTG CATATCGGGG
2521  ATGAAAGCTG GCGCATGATG ACCACCGATA TGGCCAGTGT GCCGGTCTCC GTTATCGGGG
2581  AAGAAGTGGC TGATCTCAGC CACCGCGAAA ATGACATCAA AAACGCCATT AACCTGATGT
2641  TCTGGGGAAT ATAAATGTCA GGCATGAGAT TATCAAAAAG GATCTTCACC TAGATCCTTT
2701  TCACGTAGAA AGCCAGTCCG CAGAAACGGT GCTGACCCCG GATGAATGTC AGCTACTGGG
2761  CTATCTGGAC AAGGGAAAAC GCAAGCGCAA AGAGAAAGCA GGTAGCTTGC AGTGGGCTTA
2821  CATGGCGATA GCTAGACTGG GCGGTTTTAT GGACAGCAAG CGAACCGGAA TTGCCAGCTG
2881  GGGCGCCCTC TGGTAAGGTT GGAAGCCCT GCAAAGTAAA CTGGATGGCT TTCTCGCCGC
2941  CAAGGATCTG ATGGCGCAGG GGATCAAGCT CTGATCAAGA GACAGGATGA GGATCGTTTC
```

Figure 5-1

```
3001  GCATGATTGA ACAAGATGGA TTGCACGCAG GTTCTCCGGC CGCTTGGGTG GAGAGGCTAT
3061  TCGGCTATGA CTGGGCACAA CAGACAATCG GCTGCTCTGA TGCCGCCGTG TTCCGGCTGT
3121  CAGCGCAGGG GCGCCCGGTT CTTTTTGTCA AGACCGACCT GTCCGGTGCC CTGAATGAAC
3181  TGCAAGACGA GGCAGCGCGG CTATCGTGGC TGGCCACGAC GGGCGTTCCT TGCGCAGCTG
3241  TGCTCGACGT TGTCACTGAA GCGGGAAGGG ACTGGCTGCT ATTGGGCGAA GTGCCGGGGC
3301  AGGATCTCCT GTCATCTCAC CTTGCTCCTG CCGAGAAAGT ATCCATCATG GCTGATGCAA
3361  TGCGGCGGCT GCATACGCTT GATCCGGCTA CCTGCCCATT CGACCACCAA GCGAAACATC
3421  GCATCGAGCG AGCACGTACT CGGATGGAAG CCGGTCTTGT CGATCAGGAT GATCTGGACG
3481  AAGAGCATCA GGGGCTCGCG CCAGCCGAAC TGTTCGCCAG GCTCAAGGCG AGCATGCCCG
3541  ACGGCGAGGA TCTCGTCGTG ACCCATGGCG ATGCCTGCTT GCCGAATATC ATGGTGGAAA
3601  ATGGCCGCTT TTCTGGATTC ATCGACTGTG GCCGGCTGGG TGTGGCGGAC CGCTATCAGG
3661  ACATAGCGTT GGCTACCCGT GATATTGCTG AAGAGCTTGG CGGCGAATGG GCTGACCGCT
3721  TCCTCGTGCT TTACGGTATC GCCGCTCCCG ATTCGCAGCG CATCGCCTTC TATCGCCTTC
3781  TTGACGAGTT CTTCTGAATT ATTAACGCTT ACAATTTCCT GATGCGGTAT TTTCTCCTTA
3841  CGCATCTGTG CGGTATTTCA CACCGCATAC AGGTGGCACT TTTCGGGGAA ATGTGCGCGG
3901  AACCCCTATT TGTTTATTTT TCTAAATACA TTCAAATATG TATCCGCTCA TGAGACAATA
3961  ACCCTGATAA ATGCTTCAAT AATAGCACGT GAGGAGGGCC ACCATGGCCA AGTTGACCAG
4021  TGCCGTTCCG GTGCTCACCG CGCGCGACGT CGCCGGAGCG GTCGAGTTCT GGACCGACCG
4081  GCTCGGGTTC TCCCGGGACT TCGTGGAGGA CGACTTCGCC GGTGTGGTCC GGGACGACGT
4141  GACCCTGTTC ATCAGCGCGG TCCAGGACCA GGTGGTGCCG GACAACACCC TGGCCTGGGT
4201  GTGGGTGCGC GGCCTGGACG AGCTGTACGC CGAGTGGTCG GAGGTCGTGT CCACGAACTT
4261  CCGGGACGCC TCCGGGCCGG CCATGACCGA GATCGGCGAG CAGCCGTGGG GGCGGGAGTT
4321  CGCCCTGCGC GACCCGGCCG GCAACTGCGT GCACTTCGTG GCCGAGGAGC AGGACTGACA
4381  CGTGCTAAAA CTTCATTTTT AATTTAAAAG GATCTAGGTG AAGATCCTTT TTGATAATCT
4441  CATGACCAAA ATCCCTTAAC GTGAGTTTTC GTTCCACTGA GCGTCAGACC CCGTAGAAAA
4501  GATCAAAGGA TCTTCTTGAG ATCCTTTTTT TCTGCGCGTA ATCTGCTGCT TGCAAACAAA
4561  AAAACCACCG CTACCAGCGG TGGTTTGTTT GCCGGATCAA GAGCTACCAA CTCTTTTTCC
4621  GAAGGTAACT GGCTTCAGCA GAGCGCAGAT ACCAAATACT GTCCTTCTAG TGTAGCCGTA
4681  GTTAGGCCAC CACTTCAAGA ACTCTGTAGC ACCGCCTACA TACCTCGCTC TGCTAATCCT
4741  GTTACCAGTG GCTGCTGCCA GTGGCGATAA GTCGTGTCTT ACCGGGTTGG ACTCAAGACG
4801  ATAGTTACCG GATAAGGCGC AGCGGTCGGG CTGAACGGGG GGTTCGTGCA CACAGCCCAG
4861  CTTGGAGCGA ACGACCTACA CCGAACTGAG ATACCTACAG CGTGAGCTAT GAGAAAGCGC
4921  CACGCTTCCC GAAGGGAGAA AGGCGGACAG GTATCCGGTA AGCGGCAGGG TCGAACAGG
4981  AGAGCGCACG AGGGAGCTTC CAGGGGGAAA CGCCTGGTAT CTTTATAGTC CTGTCGGGTT
5041  TCGCCACCTC TGACTTGAGC GTCGATTTTT GTGATGCTCG TCAGGGGGGC GGAGCCTATG
5101  GAAAAACGCC AGCAACGCGG CCTTTTTACG GTTCCTGGC TTTTGCTGGC CTTTTGCTCA
5161  CATGTTCTTT CCTGCGTTAT CCCCTGATTC TGTGGATAAC CGTATTACCG CCTTTGAGTG
5221  AGCTGATACC GCTCGCCGCA GCCGAACGAC CGAGCGCAGC GAGTCAGTGA GCGAGGAAGC
5281  GGAAG
```

Figure 5-2

FIGURE 6 Construct 7 DNA Sequence 5650 bp;
Composition  1372 A; 1333 C; 1516 G; 1429 T; 0 OTHER
Percentage:  24% A;  24% C;  27% G;  25% T; 0%OTHER Molecular Weight (kDa): ssDNA: 1747.85   dsDNA: 3483.2
ORIGIN

```
   1 GGATCGATCC GGCTGTGGAA TGTGTGTCAG TTAGGGTGTG GAAAGTCCCC AGGCTCCCCA
  61 GCAGGCAGAA GTATGCAAAG CATGCATCAA GCTTGGTACC GAGCTCGGAT CCACTAGTAA
 121 CGGCCGCCAG TGTGCTGGAA TTCGCCCTTA TTTAAATGGA GCCACAGCTG GTTTCTTTTA
 181 TTATTTGGGT GGAACCAATC AATTGTTTGG TCCAGCTCAG GTTGGGGGT GAAGTACCTG
 241 GAGTGGTAGG TAAAGGGCTG CCTTATGGTG TGGCGGGAGG AGTAGTTAAT ATAGGGGTCA
 301 TAGGCCAAGT TGGTGGAGGG GGTTACAAAG TTGGCATCCA AGATAACAAC AGTGGACCCA
 361 ACACCTCTTT GATTAGAGGT GATGGGGTCT CTGGGGTAAA ATTCATATTT AGCCTTTCTA
 421 ATACGGTAGT ATTGGAAAGG TAGGGGTAGG GGGTTGGTGC CGCCTGAGGG GGGCAGGAAC
 481 TGGCCGATGT TGAATTTGAG GTAGTTAACA TTCCAAGATG GCTGCGAGTA TCCTCCTTTT
 541 ATGGTGAGTA CAAATTCTGT AGAAAGGCGG GAATTGAAGA TACCCGTCTT TCGGCGCCAT
 601 CTGTAACGGT TTCTGAAGGC GGGGTGTGCC AAATATGGTC TTCTCCGGAG GATGTTTCCA
 661 AGATGGCTGC GGGGCGGGT CCTTCTTCTG CGGTAACGCC TCCTTGGCCA CGTCATCCTA
 721 TAAAAGTGAA AGAAGTGCGC TGCTGTAGTA TTACCAGCGC ACTTCGGCAG CGGCAGCACC
 781 TCGGCAGCGT CAGTGAAAAT GCCAAGCAAG AAAAGCGGCC CGCAACCCCA TAAGAGGTGG
 841 GTGTTCACCC TTAATAATCC TTCCGAGGAG GAGAAAAACA AAATACGGGA GCTTCCAATC
 901 TCCCTTTTTG ATTATTTTGT TTGCGGAGAG GAAGGTTTGG AAGAGGGTAG AACTCCTCAC
 961 CTCCAGGGGT TTGCGAATTT TGCTAAGAAG CAGACTTTTA ACAAGGTGAA GTGGTATTTT
1021 GGTGCCCGCT GCCACATCGA GAAAGCGAAA GGAACCGACC AGCAGAATAA AGAATACTGC
1081 AGTAAAGAAG GCCACATACT TATCGAGTGT GGAGCTCCGC GGAACCAGGG GAAGCGCAGC
1141 GACCTGTCTA CTGCTGTGAG TACCCTTTTG GAGACGGGGT CTTTGGTGAC TGTAGCCGAG
1201 CAGTTCCCTG TAACGTATGT GAGAAATTTC CGCGGGCTGG CTGAACTTTT GAAAGTGAGC
1261 GGGAAGATGC AGCAGCGTGA TTGGAAGACA GCTGTACACG TCATAGTGGG CCCGCCCGGT
1321 TGTGGGAAGA GCCAGTGGGC CCGTAATTTT GCTGAGCCTA GGGACACCTA CTGGAAGCCT
1381 AGTAGAAATA AGTCGTCGGA TGGATATCAT GGAGAAGAAG TTGTTGTTTT GGATGATTTT
1441 TATGGCTGGT TACCTTGGGA TGATCTACTG AGACTGTGTG ACCGGTATCC ATTGACTGTA
1501 GAGACTAAAG GGGGTACTGT TCCTTTTTTG GCCCGCAGTA TTTTGATTAC CAGCAATCAG
1561 GCCCCCCAGG AATGGTACTC CTCAACTGCT GTCCAGCTG TAGAAGCTCT CTATCGGAGG
1621 ATTACTACTT TGCAATTTTG GAAGACTGCT GGAGAACAAT CCACGGAGGT ACCCGAAGGC
1681 CGATTTGAAG CAGTGGACCC ACCCTGTGCC CTTTTCCCAT ATAAAATAAA TTACTGAGTC
1741 TTTTTTGTTA TCACATCGTA ATGGTTTTTA TTTTTATTTA TTTAGAGGGT CTTTTAGGAT
1801 AAATTCTCTG AATTGTACAT AAATAGTCAG CCTTACCACA TAATTTGGG CTGTGGCTGC
1861 ATTTGGAGC GCATAGCCGA GGCCTGTGTG CTCGACATTG GTGTGGGTAT TTAAATAAGG
1921 GCGAATTCTG CAGATATCCA TCACACTGGC GGCCGCTCGA GTCTAGAGGG CCCGTTTAAA
1981 CCCGCTGATC AGCCTCGACT GTGCCTTCTA GTTGCCAGCC ATCTGTTGTT TGCCCCTCCC
2041 CCGTGCCTTC CTTGACCCTG GAAGGTGCCA CTCCCACTGT CCTTTCCTAA TAAAATGAGG
2101 AAATTGCATC GCATTGTCTG AGTAGGTGTC ATTCTATTCT GGGGGGTGGG GTGGGGCAGG
2161 ACAGCAAGGG GGAGGATTGG GAAGACAATA GCAGGCATGC TGGGGATGCG GTGGGCTCTA
2221 TGGCTTCTGA GGCGGAAAGA ACCAGCATGT GAGCAAAAGG CCAGCAAAAG GCCAGGAACC
2281 GTAAAAAGGC CGCGTTGCTG GCGTTTTTCC ATAGGCTCCG CCCCCCTGAC GAGCATCACA
2341 AAAATCGACG CTCAAGTCAG AGGTGGCGAA ACCCGACAGG ACTATAAAGA TACCAGGCGT
2401 TTCCCCCTGG AAGCTCCCTC GTGCGCTCTC CTGTTCCGAC CCTGCCGCTT ACCGGATACC
2461 TGTCCGCCTT TCTCCCTTCG GGAAGCGTGG CGCTTTCTCA TAGCTCACGC TGTAGGTATC
2521 TCAGTTCGGT GTAGGTCGTT CGCTCCAAGC TGGGCTGTGT GCACGAACCC CCCGTTCAGC
2581 CCGACCGCTG CGCCTTATCC GGTAACTATC GTCTTGAGTC AACCCGGTA AGACACGACT
2641 TATCGCCACT GGCAGCAGCC ACTGGTAACA GGATTAGCAG AGCGAGGTAT GTAGGCGGTG
2701 CTACAGAGTT CTTGAAGTGG TGGCCTAACT ACGGCTACAC TAGAAGAACA GTATTTGGTA
2761 TCTGCGCTCT GCTGAAGCCA GTTACCTTCG GAAAAAGAGT TGGTAGCTCT TGATCCGGCA
2821 AACAAACCAC CGCTGGTAGC GGTGGTTTTT TTGTTTGCAA GCAGCAGATT ACGCGCAGAA
```

Figure 6-1

```
2881  AAAAAGGATC  TCAAGAAGAT  CCTTTGATCT  TTTCTACGGG  GTCTGACGCT  CAGTGGAACG
2941  AAAACTCACG  TTAAGGGATT  TTGGTCATGA  CATTAACCTA  TAAAAATAGG  CGTATCACGA
3001  GGCCCTTTCG  TCTCGCGCGT  TTCGGTGATG  ACGGTGAAAA  CCTCTGACAC  ATGCAGCTCC
3061  CGGAGACGGT  CACAGCTTGT  CTGTAAGCGG  ATGCCGGGAG  CAGACAAGCC  CGTCAGGGCG
3121  CGTCAGCGGG  TGTTGGCGGG  TGTCGGGGCT  GGCTTAACTA  TGCGGCATCA  GAGCAGATTG
3181  TACTGAGAGT  GCACCATATG  CGGTGTGAAA  TACCGCACAG  ATGCGTAAGG  AGAAAATACC
3241  GCATCAGGAC  GCGCCCTGTA  GCGGCGCATT  AAGCGCGGCG  GGTGTGGTGG  TTACGCGCAG
3301  CGTGACCGCT  ACACTTGCCA  GCGCCCTAGC  GCCCGCTCCT  TTCGCTTTCT  TCCCTTCCTT
3361  TCTCGCCACG  TTCGCCGGCT  TTCCCCGTCA  AGCTCTAAAT  CGGGGGCTCC  CTTTAGGGTT
3421  CCGATTTAGT  GCTTTACGGC  ACCTCGACCC  CAAAAAACTT  GATTAGGGTG  ATGGTTCACG
3481  TAGTGGGCCA  TCGCCCTGAT  AGACGGTTTT  TCGCCCTTTG  ACGTTGGAGT  CCACGTTCTT
3541  TAATAGTGGA  CTCTTGTTCC  AAACTGGAAC  AACACTCAAC  CCTATCTCGG  TCTATTCTTT
3601  TGATTTATAA  GGGATTTTGC  CGATTTCGGC  CTATTGGTTA  AAAAATGAGC  TGATTTAACA
3661  AAAATTTAAC  GCGAATTTTA  ACAAAATATT  AACGCTTACA  ATTTCCATTC  GCCATTCAGG
3721  CTGAACTAGA  TCTAGAGTCC  GTTACATAAC  TTACGGTAAA  TGGCCCGCCT  GGCTGACCGC
3781  CCAACGACCC  CCGCCCATTG  ACGTCAATAA  TGACGTATGT  TCCCATAGTA  ACGCCAATAG
3841  GGACTTTCCA  TTGACGTCAA  TGGGTGGAGT  ATTTACGGTA  AACTGCCCAC  TTGGCAGTAC
3901  ATCAAGTGTA  TCATATGCCA  AGTACGCCCC  CTATTGACGT  CAATGACGGT  AAATGGCCCG
3961  CCTGGCATTA  TGCCCAGTAC  ATGACCTTAT  GGGACTTTCC  TACTTGGCAG  TACATCTACG
4021  TATTAGTCAT  CGCTATTACC  ATGGTGATGC  GGTTTTGGCA  GTACATCAAT  GGGCGTGGAT
4081  AGCGGTTTGA  CTCACGGGGA  TTTCCAAGTC  TCCACCCCAT  TGACGTCAAT  GGGAGTTTGT
4141  TTTGGCACCA  AAATCAACGG  GACTTTCCAA  AATGTCGTAA  CAACTCCGCC  CCATTGACGC
4201  AAATGGGCGG  TAGGCGTGTA  CGGTGGGAGG  TCTATATAAG  CAGAGCTCGT  TTAGTGAACC
4261  GTCAGATCGC  CTGGAGACGC  CATCCACGCT  GTTTTGACCT  CCATAGAAGA  CACCGGGACC
4321  GATCCAGCCT  CCGCGGCCGG  GAACGGTGCA  TTGGAACGGA  CCGTGTTGAC  AATTAATCAT
4381  CGGCATAGTA  TATCGGCATA  GTATAATACG  ACAAGGTGAG  GAACTAAACC  ATGGCTAGCA
4441  AAGGAGAAGA  ACTTTTCACT  GGAGTTGTCC  CAATTCTTGT  TGAATTAGAT  GGTGATGTTA
4501  ATGGGCACAA  ATTTTCTGTC  AGTGGAGAGG  GTGAAGGTGA  TGCTACATAC  GGAAAGCTTA
4561  CCCTTAAATT  TATTTGCACT  ACTGGAAAAC  TACCTGTTCC  ATGGCCAACA  CTTGTCACTA
4621  CTTTCTCTTA  TGGTGTTCAA  TGCTTTTCCC  GTTATCCGGA  TCATATGAAA  CGGCATGACT
4681  TTTTCAAGAG  TGCCATGCCC  GAAGGTTATG  TACAGGAACG  CACTATATCT  TTCAAAGATG
4741  ACGGGAACTA  CAAGACGCGT  GCTGAAGTCA  AGTTTGAAGG  TGATACCCTT  GTTAATCGTA
4801  TCGAGTTAAA  AGGTATTGAT  TTTAAAGAAG  ATGGAAACAT  TCTCGGACAC  AAACTCGAGT
4861  ACAACTATAA  CTCACACAAT  GTATACATCA  CGGCAGACAA  ACAAAAGAAT  GGAATCAAAG
4921  CTAACTTCAA  AATTCGCCAC  AACATTGAAG  ATGGATCCGT  TCAACTAGCA  GACCATTATC
4981  AACAAAATAC  TCCAATTGGC  GATGGCCCTG  TCCTTTTACC  AGACAACCAT  TACCTGTCGA
5041  CACAATCTGC  CCTTTCGAAA  GATCCCAACG  AAAAGCGTGA  CCACATGGTC  CTTCTTGAGT
5101  TTGTAACTGC  TGCTGGGATT  ACACATGGCA  TGGATGCCAA  GTTGACCAGT  GCCGTTCCGG
5161  TGCTCACCGC  GCGCGACGTC  GCCGGAGCGG  TCGAGTTCTG  GACCGACCGG  CTCGGGTTCT
5221  CCCGGGACTT  CGTGGAGCAC  GACTTCGCCG  GTGTGGTCCG  GGACGACGTG  ACCCTGTTCA
5281  TCAGCGCGGT  CCAGGACCAG  GTGGTGCCGG  ACAACACCCT  GGCCTGGGTG  TGGGTGCGCG
5341  GCCTGGACGA  GCTGTACGCC  GAGTGGTCGG  AGGTCGTGTC  CACGAACTTC  CGGGACGCCT
5401  CCGGGCCGGC  CATGACCGAG  ATCGGCGAGC  AGCCGTGGGG  GCGGGAGTTC  GCCCTGCGCG
5461  ACCCGGCCGG  CAACTGCGTG  CACTTCGTGG  CCGAGGAGCA  GGACTGACAC  TCGACCTCGA
5521  AACTTGTTTA  TTGCAGCTTA  TAATGGTTAC  AAATAAAGCA  ATAGCATCAC  AAATTTCACA
5581  AATAAAGCAT  TTTTTTCACT  GCATTCTAGT  TGTGGTTTGT  CCAAACTCAT  CAATGTATCT
5641  TATCATGTCT
```

Figure 6-2

SEQUENCE LISTING

<160> NUMBER OF SEQ ID NOS: 21

<210> SEQ ID NO 1
<211> LENGTH: 9
<212> TYPE: DNA
<213> ORGANISM: Geminivirus

```
<400> SEQUENCE: 1 taatattac                                                            9

<210> SEQ ID NO 2
<211> LENGTH: 9
<212> TYPE: DNA
<213> ORGANISM: Circovirus
<220> FEATURE:
<221> NAME/KEY: variation
<222> LOCATION: (3)...(3)
<223> OTHER INFORMATION: N= A or C or G or T

<400> SEQUENCE: 2 tantattac                                                            9

<210> SEQ ID NO 3
<211> LENGTH: 5
<212> TYPE: PRT
<213> ORGANISM: Circovirus

<400> SEQUENCE: 3

Phe Thr Leu Asn Asn
 1               5

<210> SEQ ID NO 4
<211> LENGTH: 5
<212> TYPE: PRT
<213> ORGANISM: Nanovirus

<400> SEQUENCE: 4

Phe Thr Leu Asn Tyr
 1               5

<210> SEQ ID NO 5
<211> LENGTH: 5
<212> TYPE: PRT
<213> ORGANISM: Geminivirus

<400> SEQUENCE: 5

Phe Leu Thr Tyr Pro
 1               5

<210> SEQ ID NO 6
<211> LENGTH: 9
<212> TYPE: PRT
<213> ORGANISM: Circovirus
<220> FEATURE:
<223> OTHER INFORMATION: Xaa = Any amino acid

<400> SEQUENCE: 6

Gly Xaa Xaa Xaa His Leu Gln Gly Phe
 1               5

<210> SEQ ID NO 7
<211> LENGTH: 5
<212> TYPE: PRT
<213> ORGANISM: Geminivirus

<400> SEQUENCE: 7

Phe Leu Thr Tyr Pro
 1               5

<210> SEQ ID NO 8
<211> LENGTH: 8
```

```
<212> TYPE: PRT
<213> ORGANISM: Geminivirus
<220> FEATURE:
<223> OTHER INFORMATION: Xaa = Any amino acid

<400> SEQUENCE: 8

Gly Xaa Xaa His Leu His Ala Leu
 1               5

<210> SEQ ID NO 9
<211> LENGTH: 8
<212> TYPE: PRT
<213> ORGANISM: Geminivirus
<220> FEATURE:
<223> OTHER INFORMATION: Xaa = Any amino acid

<400> SEQUENCE: 9

Gly Xaa Xaa His Leu His Val Leu
 1               5

<210> SEQ ID NO 10
<211> LENGTH: 7
<212> TYPE: PRT
<213> ORGANISM: Circovirus
<220> FEATURE:
<223> OTHER INFORMATION: Xaa = Any amino acid

<400> SEQUENCE: 10

Val Arg Xaa Tyr Xaa Xaa Lys
 1               5

<210> SEQ ID NO 11
<211> LENGTH: 7
<212> TYPE: PRT
<213> ORGANISM: Circovirus
<220> FEATURE:
<223> OTHER INFORMATION: Xaa = Any amino acid

<400> SEQUENCE: 11

Asn Arg Xaa Tyr Xaa Xaa Lys
 1               5

<210> SEQ ID NO 12
<211> LENGTH: 7
<212> TYPE: PRT
<213> ORGANISM: Circovirus
<220> FEATURE:
<223> OTHER INFORMATION: Xaa = Any amino acid

<400> SEQUENCE: 12

Val Lys Xaa Tyr Xaa Xaa Lys
 1               5

<210> SEQ ID NO 13
<211> LENGTH: 7
<212> TYPE: PRT
<213> ORGANISM: Circovirus
<220> FEATURE:
<223> OTHER INFORMATION: Xaa = Any amino acid

<400> SEQUENCE: 13

Asn Lys Xaa Tyr Xaa Xaa Xaa
 1               5

<210> SEQ ID NO 14
<211> LENGTH: 43
<212> TYPE: PRT
```

<210> SEQ ID NO 14
<211> LENGTH: 43
<212> TYPE: PRT
<213> ORGANISM: Circovirus
<220> FEATURE:
<223> OTHER INFORMATION: Xaa = Any amino acid

<400> SEQUENCE: 14

Gly Xaa Xaa Xaa Xaa Gly Lys Xaa Xaa Trp Ala Arg Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Asp Asp
        35                  40

<210> SEQ ID NO 15
<211> LENGTH: 43
<212> TYPE: PRT
<213> ORGANISM: Circovirus
<220> FEATURE:
<223> OTHER INFORMATION: Xaa= Any amno acid

<400> SEQUENCE: 15

Gly Xaa Xaa Xaa Xaa Gly Lys Xaa Xaa Trp Ala Arg Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Asp Asp
        35                  40

<210> SEQ ID NO 16
<211> LENGTH: 5225
<212> TYPE: DNA
<213> ORGANISM: Porcine Circovirus

<400> SEQUENCE: 16

```
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccatgattac gccaagctat     240
taggtgaca ctatagaata ctcaagctat gcatcaagct tggtaccgag ctcggatcca     300
ctagtaacgg ccgccagtgt gctggaattc gcccttattt aaatggagcc acagctggtt     360
tcttttatta tttgggtgga accaatcaat tgtttggtcc agctcaggtt tgggggtgaa     420
gtacctggag tggtaggtaa agggctgcct tatggtgtgg cggaggagt agttaatata     480
ggggtcatag gccaagttgg tgagggggt tacaaagttg gcatccaaga taacaacagt     540
ggacccaaca cctctttgat tagaggtgat ggggtctctg gggtaaaatt catatttagc     600
ctttctaata cggtagtatt ggaaaggtag gggtaggggg ttggtgccgc ctgagggggg     660
gaggaactgg ccgatgttga atttgaggta gttaacattc aagatggct gcagatatcc     720
tccttttatg gtgagtacaa attctgtaga aaggcgggaa ttgaagatac ccgtctttcg     780
gcgccatctg taacggtttc tgaaggcggg gtgtgccaaa tatggtcttc tccggaggat     840
gtttccaaga tggctgcggg ggcgggtcct tcttctgcgg taacgcctcc ttggccacgt     900
catcctataa aagtgaaaga agtgcgctgc tgtagtatta ccagcgcact tcggcagcgg     960
cagcacctcg gcagcgtcag tgaaaatgcc aagcaagaaa gcggcccgc aaccccataa    1020
gaggtgggtg ttcacccctta ataatccttc cgaggaggaa aaaacaaaa tacgggagct    1080
tccaatctcc cttttttgatt attttgtttg cggagaggaa ggtttggaag agggtagaac    1140
```

-continued

```
tcctcacctc cagggtttg cgaattttgc taagaagcag acttttaaca aggtgaagtg    1200
gtattttggt gcccgctgcc acatcgagaa agcgaaagga accgaccagc agaataaaga    1260
atactgcagt aaagaaggcc acatacttat cgagtgtgga gctccgcgga accaggggaa    1320
gcgcagcgac ctgtctactg ctgtgagtac ccttttggag acgggtcttt tggtgactgt    1380
agccgagcag ttccctgtaa cgtatgtgag aaatttccgc gggctggctg aacttttgaa    1440
agtgagcggg aagatgcagc agcgtgattg aagacagct gtacacgtca tagtgggccc    1500
gcccggttgt gggaagagcc agtgggcccg taattttgct gagcctaggg acacctactg    1560
gaagcctagt agaaataagt ggtgggatgg atatcatgga gaagaagttg ttgttttgga    1620 tgattttat ggctggttac cttgggatga tctactgaga ctgtgtgacc ggtatccatt    1680
gactgtagag actaaagggg gtactgttcc ttttttggcc cgcagtattt tgattaccag    1740
caatcaggcc cccaggaat ggtactcctc aactgctgtc ccagctgtag aagctctcta    1800
tcggaggatt actactttgc aattttggaa gactgctgga gaacaatcca cggaggtacc    1860
cgaaggccga tttgaagcag tggacccacc ctgtgccctt ttcccatata aaataaatta    1920
ctgagtcttt tttgttatca catcgtaatg gttttattt ttatttattt agagggtctt    1980
ttaggataaa ttctctgaat tgtacataaa tagtcagcct taccacataa ttttgggctg    2040
tggctgcatt ttggagcgca tagccgaggc ctgtgtgctc gacattggtg tgggtattta    2100 aaaaggggcga attctgcaga tatccatcac actggcggcc gctcgagcat gcatctagag    2160
ggcccaattc gccctatagt gagtcgtatt acaattcact ggccgtcgtt ttacaacgtc    2220
gtgactggga aaaccctggc gttacccaac ttaatcgcct tgcagcacat ccccctttcg    2280
ccagctggcg taatagcgaa gaggcccgca ccgatcgccc ttcccaacag ttgcgcagcc    2340
tatacgtacg gcagtttaag gtttacacct ataaagaga gagccgttat cgtctgtttg    2400
tggatgtaca gagtgatatt attgacacgc cggggcgacg gatggtgatc cccctggcca    2460
gtgcacgtct gctgtcagat aaagtctccc gtgaacttta cccggtggtg catatcgggg    2520
atgaaagctg gcgcatgatg accaccgata tggccagtgt gccggtctcc gttatcgggg    2580
aagaagtggc tgatctcagc caccgcgaaa atgacatcaa aaacgccatt aacctgatgt    2640 tctgggaat ataaatgtca ggcatgagat tatcaaaaag gatcttcacc tagatccttt    2700
tcacgtagaa agccagtccg cagaaacggt gctgaccccg gatgaatgtc agctactggg    2760
ctatctggac aagggaaaac gcaagcgcaa agagaaagca ggtagcttgc agtgggctta    2820
catggcgata gctagactgg gcggttttat ggacagcaag cgaaccggaa ttgccagctg    2880
gggcgccctc tggtaaggtt gggaagccct gcaaagtaaa ctggatggct ttctcgccgc    2940
caaggatctg atggcgcagg ggatcaagct ctgatcaaga gacaggatga ggatcgtttc    3000
gcatgattga acaagatgga ttgcacgcag gttctccggc cgcttgggtg gagaggctat    3060
tcggctatga ctgggcacaa cagacaatcg gctgctctga tgccgccgtg ttccggctgt    3120
cagcgcaggg gcgcccggtt cttttttgtca agaccgacct gtccggtgcc ctgaatgaac    3180
tgcaagacga ggcagcgcgg ctatcgtggc tggccacgac gggcgttcct tgcgcagctg    3240
tgctcgacgt tgtcactgaa gcgggaaggg actggctgct attgggcgaa gtgccggggc    3300
aggatctcct gtcatctcac cttgctcctg ccgagaaagt atccatcatg gctgatgcaa    3360
tgcggcggct gcatacgctt gatccggcta cctgcccatt cgaccaccaa gcgaaacatc    3420
gcatcgagcg agcacgtact cggatggaag ccggtcttgt cgatcaggat gatctggacg    3480
```

```
aagagcatca ggggctcgcg ccagccgaac tgttcgccag gctcaaggcg agcatgcccg    3540
acggcgagga tgtcgtcgtg acccatggcg atgcctgctt gccgaatatc atggtggaaa    3600
atggccgctt ttctggattc atcgactgtg gccggctggg tgtggcggac cgctatcagg    3660
acatagcgtt ggctacccgt gatattgctg aagagcttgg cggcgaatgg gctgaccgct    3720
tcctcgtgct ttacggtatc gccgctcccg attcgcagcg catcgccttc tatcgccttc    3780
ttgacgagtt cttctgaatt attaacgctt acaatttcct gatgcggtat tttctcctta    3840
cgcatctgtg cggtatttca caccgcatac aggtggcact tttcggggaa atgtgcgcgg    3900 aaccccctatt tgtttatttt tctaaataca ttcaaatatg tatccgctca tgagacaata    3960
accctgataa atgcttcaat aatagcacgt gaggagggcc accatggcca agttgaccag    4020
gctcgggttc tcccgggact cgtggagga cgacttcgcc ggtgtggtcc gggacgacgt    4080
gaccctgttc atcagcgcgg tccaggacca ggtggtgccg gacaacaccc tggcctgggt    4140
gtgggtgcgc ggcctggacg agctgtacgc cgagtggtcg gaggtcgtgt ccacgaactt    4200
ccgggacgcc tccgggccgg ccatgaccga gatcggcgag cagccgtggg gcgggagtt    4260 cgccctgcgc gacccggccg gcaactgcgt gcacttcgtg gccgaggagc aggactgaca    4320
cgtgctaaaa cttcattttt aatttaaaag gatctaggtg aagatccttt tgataatct    4380 catgaccaaa atcccttaac gtgagttttc gttccactga gcgtcagacc ccgtagaaaa    4440
gatcaaagga tcttcttgag atccttttt tctgcgcgta atctgctgct tgcaaacaaa    4500 aaaccaccg ctaccagcgg tggtttgttt gccggatcaa gagctaccaa ctcttttttcc    4560 gaaggtaact ggcttcagca gagcgcagat accaaatact gtccttctag tgtagccgta    4620
gttaggccac cacttcaaga actctgtagc accgcctaca tacctcgctc tgctaatcct    4680
gttaccagtg gctgctgcca gtggcgataa gtcgtgtctt accgggttgg actcaagacg    4740
atagttaccg gataaggcgc agcggtcggg ctgaacgggg ggttcgtgca cacagcccag    4800
cttggagcga acgacctaca ccgaactgag atacctacag cgtgagctat gagaaagcgc    4860
cacgcttccc gaagggagaa aggcggacag gtatccggta agcggcaggg tcggaacagg    4920
agagcgcacg agggagcttc caggggggaaa cgcctggtat ctttatagtc ctgtcgggtt    4980
tcgccacctc tgacttgagc gtcgattttt gtgatgctcg tcagggggc ggagcctatg    5040 gaaaaacgcc agcaacgcgg ccttttacg gttcctggc ttttgctggc cttttgctca    5100
catgttcttt cctgcgttat cccctgattc tgtggataac cgtattaccg cctttgagtg    5160
agctgatacc gctcgccgca gccgaacgac cgagcgcagc gagtcagtga gcgaggaagc    5220
ggaag                                                                5225
```

<210> SEQ ID NO 17
<211> LENGTH: 5650
<212> TYPE: DNA
<213> ORGANISM: Porcine Circovirus

<400> SEQUENCE: 17

```
ggatcgatcc ggctgtggaa tgtgtgtcag ttagggtgtg gaaagtcccc aggctcccca     60
gcaggcagaa gtatgcaaag catgcatcaa gcttggtacc gagctcggat ccactagtaa    120
cggccgccag tgtgctggaa ttcgccctta tttaaatgga gccacagctg gtttcttta    180 ttatttgggt ggaaccaatc aattgtttgg tccagctcag gtttggggt gaagtacctg    240 gagtggtagg taaagggctg cctatggtg tggcggagg agtagttaat atagggtca    300 taggccaagt tggtggaggg ggttacaaag ttggcatcca agataacaac agtggaccca    360
```

```
acacctcttt gattagaggt gatggggtct ctggggtaaa attcatatttt agcctttcta      420 atacggtagt attggaaagg taggggtagg gggttggtgc cgcctgaggg ggggaggaac      480
tggccgatgt tgaatttgag gtagttaaca ttccaagatg gctgcgagta tcctcctttt      540
atggtgagta caaattctgt agaaaggcgg gaattgaaga tacccgtctt tcggcgccat      600
ctgtaacggt ttctgaaggc ggggtgtgcc aaatatggtc ttctccggag gatgtttcca      660
agatggctgc gggggcgggt ccttcttctg cggtaacgcc tccttggcca cgtcatccta      720
taaaagtgaa agaagtgcgc tgctgtagta ttaccagcgc acttcggcag cggcagcacc      780
tcggcagcgt cagtgaaaat gccaagcaag aaaagcggcc cgcaacccca taagaggtgg      840
gtgttcaccc ttaataatcc ttccgaggag gagaaaaaca aaatacggga gcttccaatc      900 tcccttttg attatttgt ttgcggagag gaaggtttgg aagagggtag aactcctcac      960 ctccagggt ttgcgaattt tgctaagaag cagacttta acaaggtgaa gtggtatttt     1020
ggtgcccgct gccacatcga gaaagcgaaa ggaaccgacc agcagaataa agaatactgc     1080
agtaaagaag gccacatact tatcgagtgt ggagctccgc ggaaccaggg gaagcgcagc     1140
gacctgtcta ctgctgtgag tacccttttg gagacggggt ctttggtgac tgtagccgag     1200
cagttccctg taacgtatgt gagaaatttc cgcgggctgg ctgaacttt gaaagtgagc     1260 gggaagatgc agcagcgtga ttggaagaca gctgtacacg tcatagtggg cccgcccggt     1320
tgtgggaaga gccagtgggc ccgtaattt gctgagccta gggacaccta ctggaagcct     1380
agtagaaata agtggtggga tggatatcat ggagaagaag ttgttgtttt ggatgatttt     1440
tatggctggt taccttggga tgatctactg agactgtgtg accggtatcc attgactgta     1500
gagactaaag ggggtactgt tccttttttg gcccgcagta ttttgattac cagcaatcag     1560
gccccccagg aatggtactc ctcaactgct gtcccagctg tagaagctct ctatcggagg     1620
attactactt tgcaattttg gaagactgct ggagaacaat ccacggaggt acccgaaggc     1680
cgatttgaag cagtggaccc accctgtgcc cttttcccat ataaaataaa ttactgagtc     1740 tttttttgtta tcacatcgta atggtttta ttttatttta tttagagggt cttttaggat     1800
aaattctctg aattgtacat aaatagtcag ccttaccaca taattttggg ctgtggctgc     1860 atttgagc gcatagccga ggcctgtgtg ctcgacattg gtgtgggtat ttaaataagg     1920
gcgaattctg cagatatcca tcacactggc ggccgctcga gtctagaggg cccgtttaaa     1980
cccgctgatc agcctcgact gtgccttcta gttgccagcc atctgttgtt tgcccctccc     2040
ccgtgccttc cttgaccctg gaaggtgcca ctcccactgt cctttcctaa taaaatgagg     2100
aaattgcatc gcattgtctg agtaggtgtc attctattct gggggtggg gtggggcagg     2160 acagcaaggg ggaggattgg gaagacaata gcaggcatgc tggggatgcg gtgggctcta     2220
tggcttctga ggcggaaaga accagcatgt gagcaaaagg ccagcaaaag gccaggaacc     2280
gtaaaaaggc cgcgttgctg gcgttttcc ataggctccg ccccctgac gagcatcaca     2340 aaaatcgacg ctcaagtcag aggtggcgaa acccgacagg actataaaga taccaggcgt     2400 ttcccctgg aagctccctc gtgcgctctc ctgttccgac cctgccgctt accggatacc     2460
tgtccgcctt tctcccttcg ggaagcgtgg cgctttctca tagctcacgc tgtaggtatc     2520
tcagttcggt gtaggtcgtt cgctccaagc tgggctgtgt gcacgaaccc cccgttcagc     2580
ccgaccgctg cgccttatcc ggtaactatc gtcttgagtc caacccggta agacacgact     2640
tatcgccact ggcagcagcc actggtaaca ggattagcag agcgaggtat gtaggcggtg     2700
```

```
ctacagagtt cttgaagtgg tggcctaact acggctacac tagaagaaca gtatttggta    2760
tctgcgctct gctgaagcca gttaccttcg gaaaaagagt tggtagctct tgatccggca    2820
aacaaaccac cgctggtagc ggtggttttt ttgtttgcaa gcagcagatt acgcgcagaa    2880
aaaaaggatc tcaagaagat cctttgatct tttctacggg gtctgacgct cagtggaacg    2940
aaaactcacg ttaagggatt ttggtcatga cattaaccta taaaaatagg cgtatcacga    3000 ggcccttteg tctcgcgcgt ttcggtgatg acggtgaaaa cctctgacac atgcagctcc    3060
cggagacggt cacagcttgt ctgtaagcgg atgccgggag cagacaagcc cgtcagggcg    3120
cgtcagcggg tgttggcggg tgtcgggct ggcttaacta tgcggcatca gagcagattg    3180
tactgagagt gcaccatatg cggtgtgaaa taccgcacag atgcgtaagg agaaaatacc    3240
gcatcaggac gcgccctgta gcggcgcatt aagcgcggcg ggtgtggtgg ttacgcgcag    3300
cgtgaccgct acacttgcca gcgccctagc gcccgctcct ttcgctttct tcccttcctt    3360
tctcgccacg ttcgccggct ttccccgtca agctctaaat cgggggctcc ctttagggtt    3420
ccgatttagt gctttacggc acctcgaccc caaaaaactt gattagggtg atggttcacg    3480
tagtgggcca tcgccctgat agacggtttt tcgccctttg acgttggagt ccacgttctt    3540
taatagtgga ctcttgttcc aaactggaac aacactcaac cctatctcgg tctattcttt    3600
tgatttataa gggattttgc cgatttcggc ctattggtta aaaaatgagc tgatttaaca    3660
aaaatttaac gcgaatttta acaaaatatt aacgcttaca atttccattc gccattcagg    3720
ctgaactaga tctagagtcc gttacataac ttacggtaaa tggcccgcct ggctgaccgc    3780
ccaacgaccc ccgcccattg acgtcaataa tgacgtatgt tcccatagta acgccaatag    3840
ggactttcca ttgacgtcaa tgggtggagt atttacggta aactgcccac ttggcagtac    3900
atcaagtgta tcatatgcca agtacgcccc ctattgacgt caatgacggt aaatggcccg    3960
cctggcatta tgcccagtac atgaccttat gggactttcc tacttggcag tacatctacg    4020
tattagtcat cgctattacc atggtgatgc ggttttggca gtacatcaat gggcgtggat    4080
agcggtttga ctcacgggga tttccaagtc tccaccccat tgacgtcaat gggagtttgt    4140
tttggcacca aaatcaacgg gactttccaa aatgtcgtaa caactccgcc ccattgacgc    4200
aaatgggcgg taggcgtgta cggtgggagg tctatataag cagagctcgt ttagtgaacc    4260
gtcagatcgc ctggagacgc catccacgct gttttgacct ccatagaaga caccgggacc    4320
gatccagcct ccgcggccgg gaacggtgca ttggaacgga ccgtgttgac aattaatcat    4380
cggcatagta tatcggcata gtataatacg acaaggtgag gaactaaacc atggctagca    4440
aaggagaaga acttttcact ggagttgtcc caattcttgt tgaattagat ggtgatgtta    4500
atgggcacaa attttctgtc agtggagagg gtgaaggtga tgctacatac ggaaagctta    4560
cccttaaatt tatttgcact actgggaaaac tacctgttcc atggccaaca cttgtcacta    4620 cttttctctta tggtgttcaa tgcttttccc gttatccgga tcatatgaaa cggcatgact    4680
ttttcaagag tgccatgccc gaaggttatg tacaggaacg cactatatct ttcaaagatg    4740
acggaactaa caagacgcgt gctgaagtca gtttgaagg tgatacccctt gttaatcgta    4800 tcgagttaaa aggtattgat tttaaagaag atggaaacat tctcggacac aaactcgagt    4860
acaactataa ctcacacaat gtatacatca cggcagacaa acaaaagaat ggaatcaaag    4920
ctaacttcaa aattcgccac aacattgaag atggatccgt tcaactagca gaccattatc    4980
aacaaaatac tccaattggc gatggccctg tccttttacc agacaaccat tacctgtcga    5040
cacaatctgc cctttcgaaa gatcccaacg aaaagcgtga ccacatggtc cttcttgagt    5100
```

-continued

```
ttgtaactgc tgctgggatt acacatggca tggatgccaa gttgaccagt gccgttccgg    5160
tgctcaccgc gcgcgacgtc gccggagcgg tcgagttctg gaccgaccgg ctcgggttct    5220
cccgggactt cgtggaggac gacttcgccg gtgtggtccg ggacgacgtg accctgttca    5280
tcagcgcggt ccaggaccag gtggtgccgg acaacaccct ggcctgggtg tgggtgcgcg    5340
gcctggacga gctgtacgcc gagtggtcgg aggtcgtgtc cacgaacttc cgggacgcct    5400
ccgggccggc catgaccgag atcggcgagc agccgtgggg cgggagttc gccctgcgcg     5460 accccggccgg caactgcgtg cacttcgtgg ccgaggagca ggactgacac tcgacctcga   5520
aacttgttta ttgcagctta taatggttac aaataaagca atagcatcac aaatttcaca    5580
aataaagcat tttttcact gcattctagt tgtggtttgt ccaaactcat caatgtatct     5640
tatcatgtct                                                           5650
```

<210> SEQ ID NO 18
<211> LENGTH: 25
<212> TYPE: DNA
<213> ORGANISM: Porcine Circovirus

<400> SEQUENCE: 18

```
tttatttaaa tggagccaca gctgg                                          25
```

<210> SEQ ID NO 19
<211> LENGTH: 26
<212> TYPE: DNA
<213> ORGANISM: Porcine Circovirus

<400> SEQUENCE: 19

```
tttatttaat acccacacca atgtcg                                         26
```

<210> SEQ ID NO 20
<211> LENGTH: 26
<212> TYPE: DNA
<213> ORGANISM: Porcine Circovirus

<400> SEQUENCE: 20

```
accatgccaa gcaagaaaag cggccc                                         26
```

<210> SEQ ID NO 21
<211> LENGTH: 23
<212> TYPE: DNA
<213> ORGANISM: Porcine Circovirus

<400> SEQUENCE: 21

```
ttttcactga cgctgccgag gtg                                            23
```

ROLLING CIRCLE REPLICON EXPRESSION VECTOR

This is a continuation of Ser. No. 09/505,477 filed on Feb. 16, 2000, now abandoned.

FIELD OF THE INVENTION

This invention relates to the field of single stranded circular DNA (ssDNA) viruses that infect eukaryotic hosts. In particular this invention relates to viral vectors having utility in gene expression in a eukaryotic host. Among the viruses in this field are the Geminiviruses, Nanoviruses, and Circoviruses.

BACKGROUND OF THE INVENTION

The single stranded circular DNA (ssDNA) viruses that infect eukaryotic hosts belong to several different virus taxonomic families (Van Regenmortel et al., 1999; Pringle, 1999). Circoviruses, Circinoviruses (Mushahwar et al., 1999), Gyroviruses and Parvoviruses infect vertebrates; some Parvoviruses (subfamily Densovirinae) also infect invertebrate hosts while Geminiviruses and viruses in the genus Nanovirus infect plants. There is recent evidence that the viruses currently classified as Circoviruses evolved from Nanoviruses and have switched from a plant to a vertebrate host (Gibbs and Weiller, 1999).

Geminiviruses, Nanoviruses, and Circoviruses are all small circular ssDNA viruses that appear to be fairly closely related, in that they use the same basic rolling-circle mechanism of replication (RCR) and employ very similar life cycle strategies. Recently published data indicate that some plant RCR viruses—dicot-infecting begomoviruses and at least one Nanovirus genomic component even co-exist in some plant infections, with the geminiviral component of the infection presumably providing movement and propagation functions for the Nanovirus element, which functions as a sort of autonomously replicating satellite virus (Mansoor et al., 1999; Saunders and Stanley, 1999). The genomes of all of the plant RCR viruses, and related vertebrate-infecting Circoviruses are small, single-stranded and circular. The Geminiviruses have mono- or bi-partite genomes, with each genomic component between 2.5 and 3.0-kb. The Nanoviruses have multipartite genomes, generally with at least six, and up to ten, circular subgenomic ssDNAs, each of about 1.0-kb (Katul et al., 1998; Boevink et al., 1995; Burns et al., 1995). The Circoviruses PCV and BFDV have circular ssDNA genomes between 1.75- and 2.0-kb that encode at least two proteins. It is hypothesized that the PCV and BFDV genomes evolved after a recombination event between at least two Nanovirus subgenomic component and a vertebrate RNA-infecting virus which contributed a small portion of the new virus's replication associated protein.

The life cycle of the plant RCR viruses and Circoviruses consists of the following stages, (reviewed by Palmer and Rybicki, 1998; Hanley-Bowdoin et al., 1999):

1. Entry of the ssDNA of the virus into the cytoplasm of the host cell as virion or ssDNA-protein complex.
2. Entry of the ssDNA into the host cell nucleus. This could be a passive process, or may be mediated by the viral capsid protein and/or movement proteins (Lazarowitz, 1999)
3. Conversion of the ssDNA genome into dsDNA presumably mediated by the host DNA repair system. This conversion of the virion DNA into circular dsDNA is required for replication of all RCR replicons, as the "replicative form" (RF) dsDNA intermediate is the template for transcription of the viral genome and therefore expression of viral proteins. The RF DNA becomes associated with host histone proteins and exists as a minichromosome-like structure in the nucleus of infected cells (Abouzid et al., 1988).
4. Transcription of "early" genes—those required for viral replication—by the host RNA polymerase II complex. Production of the viral replication-associated protein (Rep) then results in initiation of RCR of the RF DNA.
5. When the viral RF form reaches a certain critical concentration level in the host cell nucleus, viral transcription regulatory proteins down-regulate transcription of early genes, and stimulate transcription of the viral "late" genes, including the structural protein/s and proteins required for dissemination of the viral genome.
6. The "late" viral proteins sequester ssDNA produced during replication, move it out of the cell nucleus and ultimately out of the infected cell, either as a ssDNA-protein complex, or as assembled virions.

The plant RCR viruses and their relatives the Circoviruses all encode a replication-associated protein (Rep) that is absolutely required for replication of the virus genomic components (Mankertz et al., 1998; Elmer et al., 1988; Hafner et al., 1997). All other proteins are dispensable for replication, and may be involved in such functions as: movement from cell-to-cell; encapsidation of the virus genome; shuttling of the virus genome between the nucleus and the cytoplasm of infected cells; transcriptional activation or repression of genes in the host or viral genome. The Rep proteins of these RCR viruses bear some distant relationship to replication initiator proteins of some ssDNA plasmids, as well as of members of the Microviridae, such as coliphage phiX174 (Ilyina and Koonin, 1992), and has led to speculation that the plant RCR viruses and Circoviruses evolved from prokaryotic ssDNA replicons. The Rep proteins of all of these replicons is a sequence specific DNA binding protein with site specific cleavage and joining activity. In all cases, Rep, probably in association with host enzymes and possibly other viral proteins (Castellano et al., 1999) binds RF DNA at specific sequences and nicks the plus strand at a specific point. In the plant RCR viruses and Circoviruses this specific point occurs within a conserved nonanucleotide sequence that occurs in the loop of a stem-loop structure in the viral intergenic region. The sequence of this nonanucleotide sequence is well conserved between all RCR viruses of plants and Circoviruses: in Geminiviruses the sequence of the nonanucleotide origin of RCR is: TAATATTAC (Palmer and Rybicki, 1998; Hanley-Bowdoin et al., 1999); in Nanoviruses (Refs) and Circoviruses the sequence is TANTATTAC (Meehan et al., 1997; Hamel et al., 1998; Morozov et al., 1998) Thus the consensus sequence for nonanucleotide origin of replication for these viruses is TANTATTAC. The Rep protein-mediated cleavage of this nonanucleotide sequence occurs between positions 7 and 8. The minimum amount of sequences that are required to be present on a DNA molecule so that it can be replicated in a reaction mediated by an RCR virus Rep protein are referred to as the RCR virus's minimal origin of replication (minimal ori). The minimal origin of replication is empirically determined, and virus species-specific; the term "minimal ori" is used interchangeably with "ori", and "origin of replication". In general, the minimal ori includes: (1) the viral stem-loop structure with TANTATTAC nonanucleotide sequence present in the loop; (2) generally, at least 90 base pairs 5' to the start of the stem-loop structure and (3) generally, at least 10, but in many cases up to 100 bases, 3' of the end of the stem-loop structure. The minimal ori is always contained within the main viral intergenic region. The main viral intergenic region (IR) is a non-coding DNA sequence that contains the stem-loop structure, TANTATTAC sequence, binding sites for the Rep protein, the minimal ori, and promoter sequences for driving transcription of viral genes in both orientations relative to the IR. In Geminiviruses of genus Begomovirus, the minimal ori is contained within the common region, a sequence within the IR that is common to both DNA A and DNA B genetic components since the sequence is required to be in present in cis for replication of both components. Likewise, the minimal ori of Nanoviruses is contained within the viral common region, present on all genome components. In Curtoviruses, the minimal ori is contained within the IR, and Mastreviruses the minimal ori is within the Long IR, but sequences in the Short IR are also required for replication. In Circoviruses the minimal ori is contained within the IR, and constitutes the stem-loop structure, TANTATTAC sequence and sequences flanking the stem-loop structure (Mankertz et al., 1997).

Replication of the plant RCR viruses and Circoviruses is entirely dependent upon a single virally-encoded replication initiator protein (Rep). Rep proteins of these viruses all contain three conserved protein motifs which are also present in replication initiator proteins from prokaryotic RCR replicons (Ilyina and Koonin, 1992; Palmer and Rybicki 1998; Mankertz et al., 1998; Meehan et al., 1997; Bassami et al., 1998; Gibbs and Weiller 1999). The function of motif I (FTLNN (SEQ ID NO:7) in Circoviruses, FTLNY (SEQ ID NO:8) in Nanoviruses and FLTYP (SEQ ID NO:9) in Geminiviruses), is unknown; Motif II (GXXXHLQGF (SEQ ID NO:10) in Circoviruses, GXXHLQGF (SEQ ID NO:11) in Nanoviruses and GXXHLH(A/V)L (SEQ ID NO:12) in Geminiviruses) and is probably involved in metal ion coordination. Motif III [(V/N)(R/K)XYXXK (SEQ ID NO:13) in all three groups] contains a conserved tyrosine residue that participates in phosphodiester bond cleavage and in the covalent linkage of Rep to the 5' terminus of the nicked nonanucleotide motif at the origin of replication. The Rep proteins of these three groups of viruses also contains a fourth conserved motif, a nucleotide triphosphate-binding domain ($GX_4GKXXWARX_{28-29}DD$) (SEQ ID NO:14) that may indicate that these proteins possess helicase activity.

Apart from their functions in RCR, Rep proteins and ancillary replication-associated "early" gene products also seem to have transcription factor activity, and are capable of controlling viral and perhaps also host gene expression. Geminivirus Rep proteins can interact with both mammalian and plant Retinoblastoma protein (Rb) homologues (Xie et al., 1995; 1996; Grafi et al., 1996; Xie et al., 1996; Ach et al., 1997). Rb belongs to a protein family that controls cell cycle progression by sequestering transcription factors necessary for entry of the cell cycle into S phase. There is also evidence that infection of plants with Geminiviruses such as tomato golden mosaic begomovirus (TGMV) is associated with an increase in the levels of proliferating cell nuclear antigen (PCNA), a DNA polymerase processivity factor required in cellular DNA replication (Nagar et al., 1995). These viruses thus appear to possess the ability to modify the host environment to one that allows viral DNA replication. At present, the exact mechanisms by which these viruses modify the host cell cycle are unclear. This could be achieved exclusively through interaction of viral proteins (such as Rep) with host proteins (such as Rb). It is also possible that transcriptional activation or repression of host genes mediated by the transcription factor activity of viral protein/s may also be involved in resetting the cellular environment to one that is permissive for viral replication.

Of this group of closely related RCR viruses, only Geminiviruses have been exploited as gene vectors in plant cells. Recombinant viral vectors that have a foreign gene inserted in place of a begomovirus coat protein can sometimes infect permissive dicotyledonous plant hosts and move systemically in infected plants (Ward et al., 1988; Hayes et al., 1988; Sudharsha et al., 1998). Vectors that contain part of the begomoviral genome, including at least three open reading frames (AC1 [=Rep],AC2 and AC3) driven by their own promoters, and containing the viral origin of replication, can replicate in transfected dicotyledonous plant cells Palmer et al., (1997). Mastrevirus-derived vectors that contain the two genes (Rep and RepA) necessary for replication of the viral genome and expression of the viral late genes, together with the viral origins of replication, can replicate in cells derived from monocotyledonous cereal plants (Palmer et al., 1997; Palmer et al., 1999).

SUMMARY OF THE INVENTION

One aspect of this invention is a rolling circle DNA replicon (RCR replicon) which replicates in a host eukaryotic cell. Another aspect of the invention is a RCR replicon which has a truncated replication cycle. Another aspect of the invention is a RCR replicon which has the following elements, present on the same DNA molecule: A Rep gene open reading frame from a virus belonging to the viral taxonomic families Geminiviridae, Circoviridae or genus Nanovirus, said Rep gene open reading frame is placed under transcriptional control of a promoter, which promoter is placed 5' of the gene; any sequences that are required to be present in cis on the rolling circle DNA replicon in order that the Rep protein might promote replication of the rolling circle DNA replicon; an expression cassette for expression of an ancillary protein that is capable of creating a cellular environment permissive for replication of the rolling circle DNA replicon in the host cell of interest; and at least one expression cassette with an RNA polymerase II promoter, a multiple cloning site, and transcription termination and polyadenylation signals suitable for transcription of RNA molecules not normally intrinsic to a geminiviral, circoviral or nanoviral genome.

Another aspect of the invention is a RCR replicon, which replicates in a host eukaryotic cell, and which has a promoter that can function in a host eukaryotic cell type of interest.

Another aspect of the invention is a RCR replicon, which replicates in a host eukaryotic cell, and which has a promoter that has some tissue, or cell-type specificity.

Another aspect of the invention is a RCR replicon for a host cell, which has a promoter that is inducible by chemical or other environmental induction.

Another aspect of the invention is a RCR replicon which replicates in a host eukaryotic cell, and which has sequences that are required to be present in cis on the rolling circle DNA replicon in order that the Rep protein might promote replication of the rolling circle DNA replicon are derived from the group consisting of Nanoviruses, Circoviruses, begomoviruses and curtoviruses.

Another aspect of the invention is an RCR replicon which replicates in a host eukaryotic cell, and which has sequences that are required to be present in cis on the rolling circle DNA replicon in order that Rep might promote the replication of the rolling circle DNA replicon. These sequences are:

(a) the origin of replication from the same virus from which the Rep protein gene was derived; said origin of replication containing the conserved stem-loop structure;
(b) a TANTATTAC sequence, where "N" may be A or C or G or T;
(c) sufficient stem-loop structure flanking sequences to provide the minimal origin of replication for the virus.

Another aspect of the invention is an RCR replicon derived from a Mastrevirus which replicates in a host eukaryotic cell, and which has sequences that are required to be present in cis on the rolling circle DNA replicon in order that Rep might promote the replication of the rolling circle DNA replicon. These sequences are:
(a) the origin of replication from the same virus from which the Rep protein gene was derived; said origin of replication containing the conserved stem-loop structure;
(b) a TANTATTAC sequence, where "N" may be A or C or G or T;
(c) sufficient stem-loop structure flanking sequences to provide the minimal origin of replication for the virus;
(d) the Short intergenic region (SIR) derived from the same Mastrevirus that provided the Rep protein gene.

Another aspect of the invention is a RCR replicon which replicates in a host eukaryotic cell, and which has an expression cassette that a) functions in expression of an ancillary protein and b) which is redundant with the Rep gene expression cassette.

Another aspect of the invention is a RCR replicon which replicates in a host eukaryotic cell, and which has an expression cassette for expression of an ancillary protein and an expression cassette driving the expression of a Rep ORF which expression cassette is from a different virus species from the group of Geminiviruses, Circoviruses and Nanoviruses.

Another aspect of the invention is a method of making a rolling circle DNA replicon which replicates in a host eukaryotic cell, comprising combining:
(a) a Rep gene open reading frame from a virus belonging to the viral taxonomic families Geminiviridae, Circoviridae or genus Nanovirus, said Rep gene open reading frame is placed under transcriptional control of a promoter, which promoter is placed 5' of the gene;
(b) any sequences that are required to be present in cis on the rolling circle DNA replicon in order that the Rep protein might promote replication of the rolling circle DNA replicon;
(c) an expression cassette for expression of an ancillary protein that is capable of creating a cellular environment permissive for replication of the rolling circle DNA replicon in the host cell of interest; and
(d) at least one expression cassette with an RNA polymerase II promoter, a multiple cloning site, and transcription termination and polyadenylation signals suitable for transcription of RNA molecules not normally intrinsic to a geminiviral, circoviral or nanoviral genome.

Another aspect of the invention is a method of making a rolling circle DNA replicon which replicates in a host eukaryotic cell which replicon has a truncated replication cycle, comprising combining:
(a) a Rep gene open reading frame from a virus belonging to the viral taxonomic families Geminiviridae, Circoviridae or genus Nanovirus, said Rep gene open reading frame is placed under transcriptional control of a promoter, which promoter is placed 5' of the gene;
(b) any sequences that are required to be present in cis on the rolling circle DNA replicon in order that the Rep protein might promote replication of the rolling circle DNA replicon;
(c) an expression cassette for expression of an ancillary protein that is capable of creating a cellular environment permissive for replication of the rolling circle DNA replicon in the host cell of interest; and
(d) at least one expression cassette with an RNA polymerase II promoter, a multiple cloning site, and transcription termination and polyadenylation signals suitable for transcription of RNA molecules not normally intrinsic to a geminiviral, circoviral or nanoviral genome.

Another aspect of the invention is a method of discovering the function of a gene or gene segment in a host eukaryotic cell, the method comprising:
(a) inserting a gene or gene segment into the multiple cloning site of the above-mentioned expression cassette in the RCR vector, such that the RNA II polymerase promoter may promote the transcription of the inserted gene or gene segment
(b) inserting the a rolling circle DNA replicon into in a host eukaryotic cell; and
(c) discovering a biochemical or phenotypic change in the in a host eukaryotic cell.

BRIEF DESCRIPTION OF THE DRAWINGS

FIG. 5 shows the DNA sequence of Construct 1: 5285 bp Composition 1216 A; 1277C;1514G;1278T; 0 OTHER Percentage: 23% A; 24% C; 29% G; 24% T; 0% OTHER. Molecular Weight (kDa): ssDNA: 1636.28 dsDNA: 3258.4 (SEQ ID NO: 1).

FIG. 6 shows the DNA sequence of Construct 7 5650 bp; Composition 1372 A; 1333 C;1516 G; 1429 T; 0 OTHER Percentage: 24% A; 24% C; 27% G; 25% T; 0% OTHER. Molecular Weight (kDa): ssDNA: 1747.85 dsDNA: 3483.2 (SEQ ID NO: 2).

DETAILED DESCRIPTION OF THE INVENTION

Figure 1:
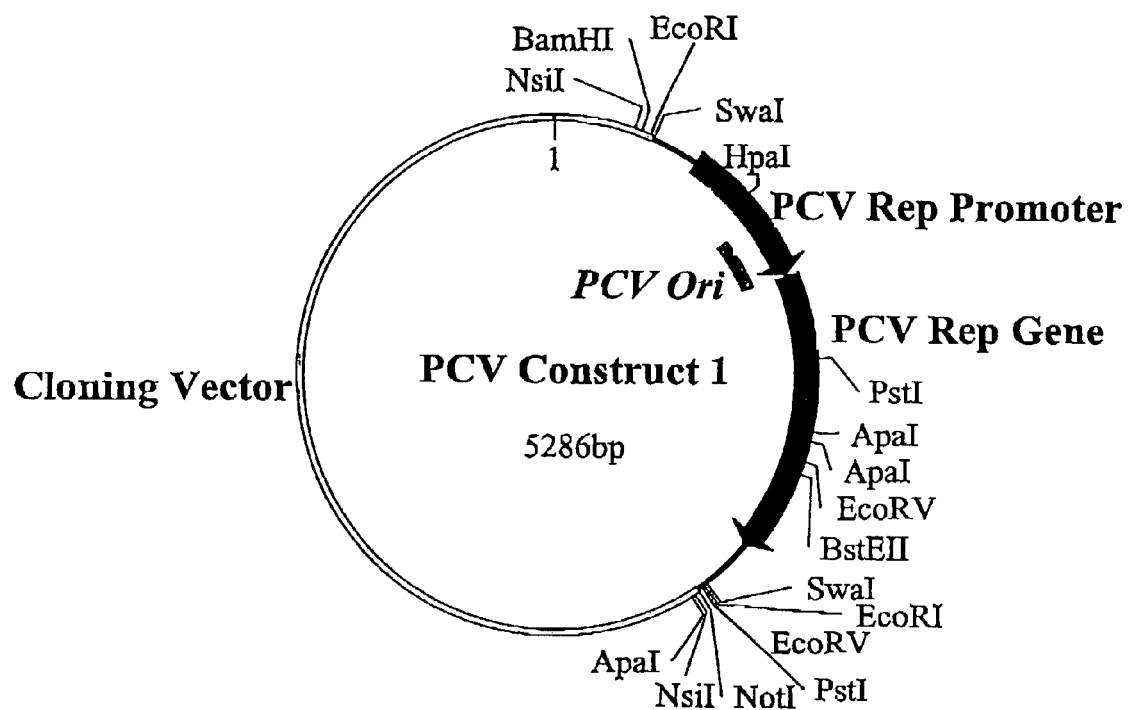
FIG. 1 shows a restriction and genetic map of Construct 1. The PCV Rep Promoter,The PCV Rep Gene with restriction sites, the PCV Ori and cloning vector are shown.

In order to facilitate understanding of the invention, certain terms used throughout are herein defined.

"BFDV" means beak and feather disease virus.

"PCV" means porcine Circovirus.

"CHO cells" means Chinese Hamster Ovary cells

"COS-7 cells" means *Cercopithecus aethiops* (African Green Monkey) kidney cells, transformed with simian virus 40 (SV40).

"D-MEM" means Dulbecco's Modified Eagle Medium.

"DpnI" is a restriction endonuclease which cuts only dam-methylated DNA.

"Buffer EC" means DNA condensation buffer.

"Effectene" is a transfection reagent, sold by Qiagen Valencia, Calif.

"GFP-zeocin" is a fusion gene made by combining the genes for green fluorescent protein and zeocin.

"G418 resistance gene" is a selectable marker gene.

"HUBEC" cell lines means human brain endothelial cell lines.

"Integrated SV40 Large T antigen-expressing gene:" The African Green Monkey Kidney cell line COS-7 contains a chromosomally-integrated SV40 virus that has a gene for the Large T antigen protein which is required for SV40 virus replication. Thus, COS-7 cells contain a chromosomally-integrated SV40 Large T antigen-expressing gene that is sufficient for episomal replication of SV40 on-containing plasmids in this cell line.

"Intergenic sequences:" The non-coding DNA sequences, wherein the viral origin of replication is situated, that are located between open reading frames of RCR viruses.

"Lipofectamine" is a cationic lipid used for transfecting mammalian cells. Life Technologies, Inc supplies Lipofectamine.

"nanonucleotide:" The sequence TANTATTAC, where "N" may be A or C or G or T. This sequence is contained within the loop of the stem-loop structure present in the origin of replication of all RCR viruses in the group of Geminiviruses, Circoviruses and Nanoviruses.

"neomycin/G418 resistance gene:" A gene that confers to the G418 antibiotic resistance.

"NsiI-NotI fragment" is a restriction fragment from Construct 1 that is used to create Construct 7.

"Passive episomal replicon inheritance:" Process where a replicon present in the nucleus of a cell is passively inherited by both daughter cells upon cell division; the replicons are not actively sequestered into each daughter cell since they do not contain a classical centromere structure, but are nevertheless inherited due to their high copy number in the original undivided cell.

"PMVC cell lines" means porcine microvascular cell lines.

"PCV genome" means the porcine Circovirus genome.

"PCV rep" The replication associated protein gene of porcine Circovirus (PCV).

"PCV RCR plasmid" A plasmid that contains the sequences derived from porcine Circovirus which allow the plasmid to replicate by rolling circle replication in a host cell.

"PK-15 cells" Porcine Kidney cell line PK-15 or PK(15). Cell line derived from kidney epithelial cells of Sus scrofa. The PK-15 cell line is persistently infected with Porcine Circovirus, type 1 (PCV).

"pCMVscript" A mammalian cell expression vector obtained from Stratagene, Inc. (La Jolla, Calif).

"pCRblunt-II TOPO vector" PCRblunt-II TOPO vector: a vector useful for cloning of PCR products sold by Invitrogen Corp. (Carlsbad, Calif.).

"PK-15SwaA and PK-15SwaB" are PCR primers used to amplify the PCV genome.

"pTracerSV40" pTracerSV40 a mammalian cell expression vector that contains an expression cassette for expression of a GFP-zeocin resistance gene; obtained from Invitrogen Corporation.

"QIAamp DNA Mini Kit" A DNA extraction kit useful for extraction of total DNA from blood and mammalian cells, sold by Qiagen Inc (Valencia, Calif.)

"Rep" means virally-encoded replication initiator protein.

"Rep gene" means a gene from an RCR virus belonging to the group of viruses from the taxonomic families Geminiviridae or Circoviridae or from the genus Nanovirus, which is essential for viral replication and which possesses a nicking and joining activity specific for the TANTATTAC sequence present in the stem loop sequence in the viral origin of replication and which is able to promote replication of an RCR virus.

"Rep gene ORF" is an open reading frame associated with a Rep gene.

"Rep protein" means replication-associated protein, a plasmid-encoded protein that functions as an activator of replication of that plasmid.

"Replicon" means any DNA sequence or molecule which possesses a replication origin and which is therefore potentially capable of being replicated in a suitable cell.

"RCR replicons" are replicons that reproduce by the rolling circle DNA replication is a mechanism.

"Rolling circle DNA replication" is a mechanism for the replication of DNA wherein one strand of a parent dsDNA molecule is nicked, and DNA synthesis proceeds by elongation of the 3'-OH end (with progressive displacement of the 5'-end), the unbroken circular strand acting as the template. The partly replicated intermediate is thus a double-stranded circular DNA with a single-stranded displaced tail.

"RCR" means rolling-circle mechanism of replication.

"Rolling circle DNA replicon" means a replicon that reproduces by the rolling circle DNA replication mechanism.

"Rolling Circle Replicon Expression Vectors" means a vector that reproduces by means of the rolling circle DNA replication method.

"RCR vector" means Rolling Circle Replicon Expression Vectors.

"RCR virus" means Rolling Circle Replicon Expression virus.

"ssDNA viruses" means single stranded circular DNA virus.

"SV40 promoter" means simian virus 40 early promoter. Simian virus 40 is a virus of the genus Polyomavirus. SV 40 was originally isolated from kidney cells of the rhesus monkey, and is common (in latent form) in such cells.

"VLPs" means virus-like particles.

THE INVENTION

This invention provides methods for designing and creating rolling circle DNA replicons for eukaryotic cells with elements from RCR viruses from the viral taxonomic families Geminiviridae, Circoviridae, and the genus Nanovirus that is as yet unassigned to a taxonomic family. We disclose methods for manipulating the genomes of these viruses so that the RCR replicons described in this invention employ only part of the replication cycle of the virus or viruses from which they were originally derived. The RCR replicons are introduced into eukaryotic host cells as double stranded DNA molecules, and thus the form in which the replicon initially enters the host is not usual for the parental virus that normally infects new host cells in an encapsidated ssDNA form. The viral "late" genes that are involved in sequestration of ssDNA, movement of viral DNA out of the host cell nucleus and assembly of viral DNA into virions are inactivated or deleted in the RCR replicons of this invention.

These RCR replicons have the following elements, present on the same DNA molecule:

1. A Rep gene ORF from a virus belonging to the viral taxonomic families Geminiviridae, Circoviridae or genus Nanovirus. This Rep gene ORF is placed under transcriptional control of a promoter, placed 5' of the gene. This promoter is chosen to be one that can function in a cell type of interest, and may additionally have some tissue, or cell-type specificity, or may be induced by the addition of a chemical or by other some other environmental induction.
2. The sequences that are required to be present in cis on the RCR replicon in order that the Rep protein might promote replication of the RCR replicon. For Nanoviruses, Circoviruses, begomoviruses and curtoviruses, this is the viral origin of replication that contains the conserved stem-loop structure, TANTATTAC nanonucleotide sequence, and flanking intergenic sequences. For mastreviruses, these include the long and short intergenic regions.
3. An expression cassette for expression of an ancillary protein that is capable of creating a cellular environment permissive for replication of the RCR replicon in the host cell of interest. This cassette may be redundant with the Rep gene expression cassette described above, or may be an expression cassette driving the expression of a Rep ORF from a different virus species from the group of Geminiviruses, Circoviruses and Nanoviruses.
4. At least one expression cassette with a RNA polymerase II promoter, a multiple cloning site, and transcription termination and polyadenylation signals suitable for transcription of RNA molecules not normally intrinsic to a geminiviral, circoviral or nanoviral genome.

Utilities:

RCR replicons are useful for discovery of the function of genes in eukaryotic hosts. RCR replicons are useful for inducing or enhancing a function or trait in a host eukaryotic cell. RCR replicons are useful for down-regulating a gene in a plant or in mammalian cells and thereby altering or even eliminating the function of that gene.

RCR replicons have several properties that will lead to the development of superior gene expression vector properties. The vector initiates a rapid replication cycle leading to earlier gene expression than standard plasmid vectors. This coupled with its self-amplifying properties will lead to sustained expression for longer periods of time as compared with standard plasmid vectors. These properties, coupled with the amplification of substrates for transcription by host machinery, will lead to greater levels and longer enduring levels of target gene expression as compared to standard plasmid vectors. The amplification of 100–1000 copies of the genome per transfected cell will lead to passive inheritance of the RCR replicon infection into daughter cells. This will lead to the development of homogeneous populations of transfected cells, all containing RCR replicons and expressed sequences, with the need for little or no biochemical selection procedures. This sustained replication in original transfected cells and resulting daughter cells will allow for long term expression experiments and novel application not available to standard plasmid vectors or other virus-based vector systems. Due to the basic aspects of the host replication system that RCR replicons require, the replicons will have virtually unlimited host range with regards to cellular replication cycles. These replicons express very few protein products outside of targeted genes or sequences for overexpression and do not perturb host cell metabolism to the same degree that other virus vectors do. All these properties give RCR replicons superior performance and make way for novel utilities not available to other plasmid or virus expression systems. For examples of several utilities, see reduction to practice section.

1. Alternative Cellular Expression System.

These vectors can be used as an alternative cellular expression vectors and perform superior to plasmid or virus-based vectors based on the following criteria: rapid replication coupled with expression driven by promoter of choice (affecting expression levels or regulation); sustained replication and passive inheritance; unlimited cellular host range; minimal host metabolism perturbation and low levels of viral protein accumulation.

2. Enhanced Immune Response in Naked DNA or Formulated DNA-based Vaccines.

RCR replicons should have sustained replication properties yielding greater levels of substrate for sustained targeted gene expression in transfected cells. The accumulation of targeted immunogen in transfected antigen presenting cells will be greater than standard plasmid vectors. Advantages over virus vectors include: Non-pathogenic, minimal host perturbation, broad cell host range, no transmission of infection to non-primarily transfected cells due to lack of packaging.

3. Mammalian-cell Based Genomics Using RCR Vectors for Gene Function Discovery.

RCR vectors will prove to be excellent gene sequence delivery tools for mammalian genomic approaches. Uses include the expression of homologous or heterologous genes in a library or targeted manner for the detection of gain of function cellular phenotypes and expression of antisense or sense gene fragments for the inhibition of targeted gene expression for assay of loss of function phenotypes.

4. Gene Therapy Applications

The sustained episomal expression in specific tissues or cells transfected by RCR replicon can allow the delivery of therapeutic or complementing (functional gene copy to complement function of a dysfunctional chromosomal copy) gene products to organisms or cells. The coupling of this activity with the ability of porcine or human brain endothelial cells lines to amplify hemopoietic stem cells without differentiation may prove to be a powerful tool to repopulate a body with new cells containing functional gene copies lacking in native organism. The coupling of these technologies will enable gene therapy to really work. For example, RCR replicon could be designed to express the glucocerebrosidase gene and transfect the hemopojetic stem cells of a patient suffering from Gaucher's disease. Once the transfected stem cells are amplified, they can be re-infused into the patient to engraft in the bone marrow. Once there, the cells will produce a range of hemopoietic cells including Kupffer cells that will be in the liver and responsible from cerebroside lipid degradation. The cells derived from stem cells transfected with the RCR vector will inherit the RCR expression replicon and now express glucocerebrosidase in the liver and now degrade the accumulating lipids that the native system is incapable of doing.

Other properties that are important in RCR vectors to succeed in gene therapy applications: sustained replication, passive episomal replicon inheritance, wide cellular and tissue host range.

5. Unique Coupling of RCR Vectors with Tissue Specific Gene Delivery Modalities.

Packaging of RCR replicon DNA in capsid proteins of viruses with specific cellular tropisms (bound by receptors on specific cell or tissue types) for targeted delivery of replicon to tissues in organisms to maximize correct immune response or therapeutic effect. For example, packaging of RCR replicons in papillomavirus virus-like particles (VLPs) would give the replicon a mucosal targeting tropism at the receptor binding step and inherent replication properties of RCR replicons will allow them to amplify and express sequences in mucosal cells. This approach will allow gene delivery for therapeutic end or immunogen delivery for generation of immune response in mucosal tissues (e.g. applications for papilloma, HIV, Herpes virus, Hepatitis B, microbial agents vaccine purposes). Likewise, integration of RCR replicon DNA into adenovirus VLPs would grant pleural tropisms for delivery of genes to advance therapeutic treatment of cystic fibrosis or other diseases. For example, following treatment of patients with DNAse, patients could receive regular treatments with VLPs containing RCR replicons containing therapeutic genes (DNAse gene) or complimenting gene (correct copies of genes causing the disease). In this manner, transient doses of replicons can transfect tissues and deliver therapeutic genes to reverse disease progression. With pleural cell shedding, new transfections with RCR replicons will be necessary to maintain the functional state of pleural tissue.

6. Whole Animal Genomics or Gene Therapy

Due to persistent replication and expression and passive inheritance of replicons in daughter cells, it should be possible to transfect pluri-potent cell lineages with replicons containing targeted genes and expect resulting daughters cells and subsequent differentiated cells (or tissues derived from them) to maintain long term expression of the gene of interest. This would allow one to transfect CD34+, CD38− hemopoietic stem cells with RCR vectors in vitro, incubation cells with PMVC or HUBEC cell lines, capable of initiating stem cell cycling and division without inducing differentiation, and then re-infuse transfected cells (now expressing novel gene product) into adult animals. All derived cells from the transfected stem cells will continue to express this novel gene function. This would allow the activities of genes to be ascertained at the entire organismal level and in the context of a variety of cell types.

Conversely, RCR vectors containing homologous or heterologous genes could be delivered to embryos of animals and the organism developing from the transfected embryo would be at least chimeric for the RCR encoded gene function or possibly homogeneous for its expression. This tool could be applied to determine gene function in the context of developing or adult organisms. Alternatively, this could be the ultimate gene therapy tool for complimenting chromosomal defects in organisms, such that the derived organism would continue to have a chromosomal defect in a gene, but it would be complemented by the persistent, episomal gene copy in the RCR vector.

7. Gene Therapy Through targeted Gene Repair.

It should be possible to perform directed mutagenesis of a DNA sequence encoded by the host chromosomal genome by encouraging homologous recombination or directed point mutation of specific host DNA sequences homologous to DNA sequences carried on the RCR replicon. Virus infection may induce all necessary factors that are involved in DNA recombination. This coupled with the generation of high levels homologous recombination substrates: single-stranded DNA during the replication cycle (thought to be more involved in DNA recombination than double stranded DNA) and high copy number of RCR genome in double-stranded DNA form, would be thought to enhance the recombinational frequencies between host chromosome and episomal replicon. For example, when Geminiviruses, containing mutations in the virus coat protein rendering the virus packaging and movement incompetent, are inoculated on transgenic plant hosts containing wild type coat protein ORF, they recombine with transgene locus to recreate a fully functional viral genome at a very high rate, Frischmuth and Stanley (1998).

EXAMPLES

The following examples further illustrate the present invention. These examples are intended merely to be illustrative of the present invention and are not to be considered as limiting.

Constructed Several Plasmids:

We constructed several plasmids to test whether RCR plasmids carrying the Rep gene and origin of replication from could replicate in different mammalian cell types.

Cloning of the Genome of PCV

We designed PCR primers to amplify parts of the genome of PCV from the strain present in PK-15 cells (Mehan et al., 1997; Genbank accession number U49186). For amplification of the whole genome of PCV, with one nucleotide mismatch from the published sequence, the following primers were used; nucleotides identical to the published sequence (accession number U49186) are underlined:

PK-15SwaA:
TTTATTTAAATGGAGCCACAGCTGG (SEQ ID NO: 3)

PK-15SwaB: TTTATTTAA-TACCCACACCAATGTCG (SEQ ID NO: 4)

In PK-15SwaB, an A has been deleted at position 9 relative to the homologous sequence in the published PCV sequence.

A 1.8-kb fragment was amplified with these primers (not shown), with total nucleic acid (100 ng) isolated from PK-15 cells used as the template for PCR. The PCR fragment was cloned into the pCRblunt-II TOPO vector, according to the manufacturer's instructions (Invitrogen). A clone containing the correct-sized insert was named construct 1 (FIG. 1).

Construct 1 (deposited to ATCC on Feb. 16, 2000, accession number PTA-1351) thus contained the whole PCV genome cloned into the Invitrogen cloning vector pCRblunt II. This construct contained the PCV rep gene under the transcriptional control of its own promoter, and has the putative coat protein inactivated by insertion of the bacterial cloning vector.

For cloning of the PCV genome and expression of its Rep gene under the control of the cytomegalovirus immediate-early promoter (CMV promoter), the PCV genome was amplified by PCR from total DNA isolated from PK-15 cells, using the following primers; nucleotides identical to the published sequence of PCV are underlined:

PCVwholerepA
ACCATGCCAAGCAAGAAAAGCGGCCC (SEQ ID NO: 5)

PCVwholerepB
TTTTCACTGACGCTGCCGAGGTG (SEQ ID NO: 6)

Figure 2:
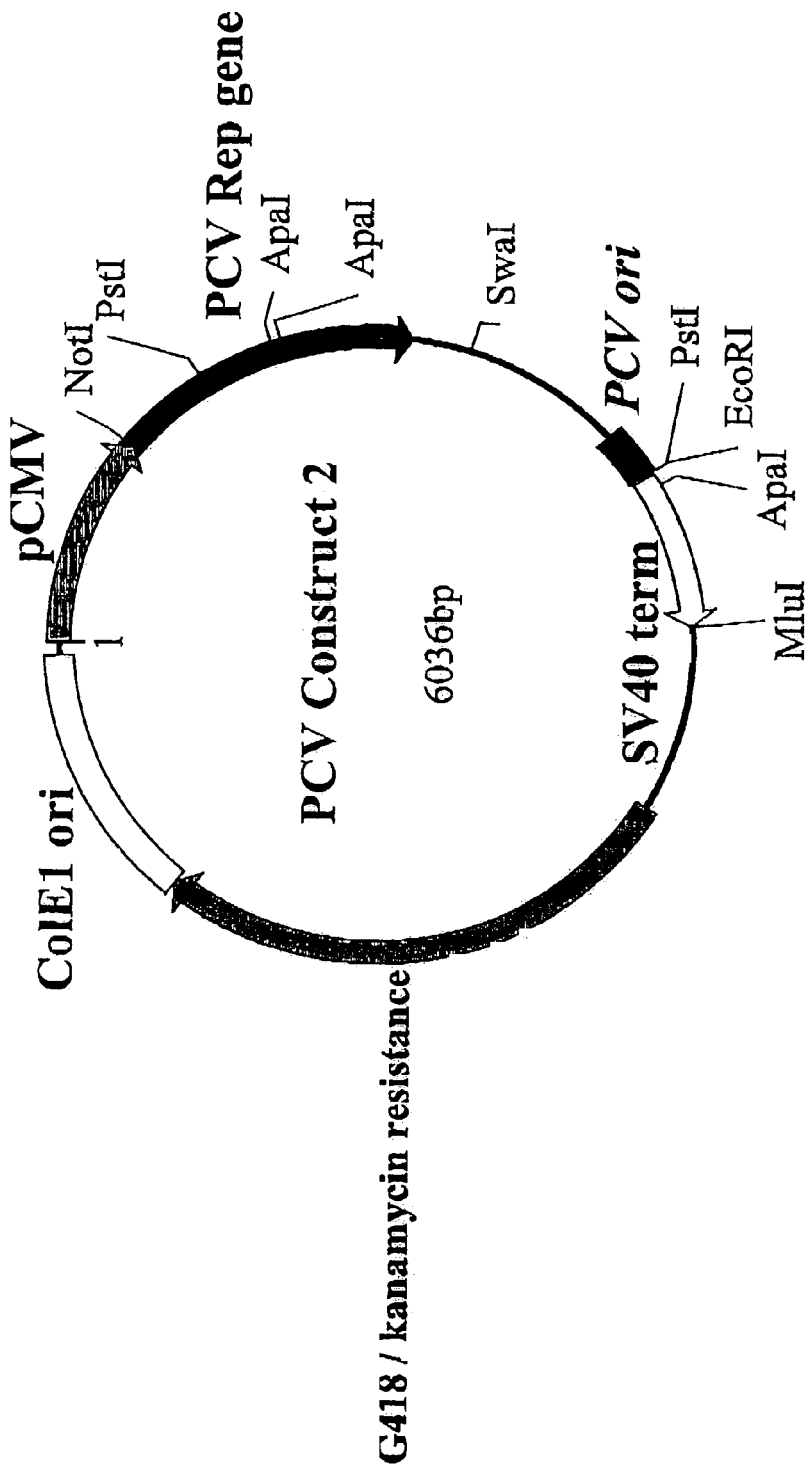
FIG. 2 shows a restriction and genetic map of Construct 2 with pCMV, pCV Rep gene, PCV Ori, and SV40 terminator with G418/kanamycin resistance gene.

A PCR product of approximately 1.8-kb was obtained after PCR amplification using these primers (not shown). This product was cloned into the vector pCMVScript according to the instructions supplied by the manufacturer (Stratagene). Construct 2, Shown in FIG. 2, contained the PCV genome cloned into the Stratagene vector, pCMVscript, such that the Rep gene was placed under the control of the cytomegalovirus immediate-early promoter (CMV promoter), with the PCV rep transcription termination and polyadenylation signal and origin of replication sequences upstream. This construct also contained a neomycin/G418 resistance gene with simian virus 40 early promoter (SV40 promoter) and origin of replication sequences, and thus should replicate episomally in COS-7 cells that have an integrated SV40 Large T antigen-expressing gene. The SV40 origin of replication will not, however, be functional in other cell types.

Construct 4 contains the PCV genome amplified with primers PK-l5SwaA and PK-15SwaB and cloned into the pCMVScript vector according to the instructions supplied by the manufacturer (Stratagene). This construct therefore contains the PCV Rep gene under the control of its own promoter in a vector which carries an SV40 origin of replication and a selectable marker gene (G418 resistance). Construct 6 is the Invitrogen pTracerSV40 (FIG. 3), which expresses a GFP-zeocin resistance gene fusion, useful because one can evaluate the success of transfection experiments by visualization of green fluorescent protein expression.

Figure 3:
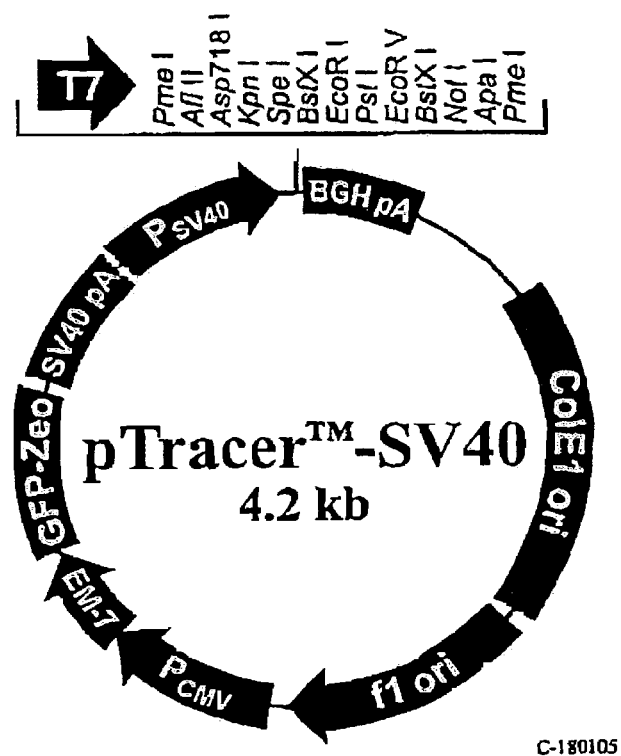
FIG. 3 shows the restriction map and genetic map of Construct 6 (p TracerSV40 from invitrogen Corp). construct 6 is the backbone of Construct 7. It contains the same GFP-zeocin expression cassette that is present in Construct 7 the NotI—NsiI fragment from Construct 1 was excised and inserted into Construct 6, replacing the SV40 promoter with the PCV fragment to generate Construct 7. The pTrace™-SV40 vector is available from Invitrogen Carlsbad, Calif.

Construct 7 (deposited in ATCC on Feb. 16, 2000, accession number PTA-1352 was derived by deleting the SV40 promoter and origin of replication sequences from pTracer SV40 (FIG. 3). The NsiI-NotI fragment from construct 1 (FIG. 1) was then cloned into the vector. This construct therefore contains the PCV Rep gene under the control of its own promoter, together with the PCV origin of replication sequences, in the context of a vector that contains a selectable and screenable marker gene (GFP-zeocin resistance), but which cannot replicate in COS-7 cells because the SV40 origin of replication sequences have been deleted.

Transfection Experiments with PCV Replicons

The RCR vectors described herein may be introduced into eukaryotic cells by one of many different protocols that are available for direct transfer of DNA into cells, including, but not limited to: electroporation, cationic lipid-mediated transfection, calcium phosphate transfection, Agrobacterium-mediated transfection, microprojectile bombardment, polyethylene glycol-mediated transfection. Several methods that are commonly used for introduction of DNA into mammalian cells are described in detail in "Current Protocols in Molecular Biology" by Ausubel et al. (1994–2000). John Wiley and Sons, Inc.

Constructs 1, 2, 4 and 6 were transfected into *Cercopithecus aethiops* (African Green Monkey) kidney cells, transformed with SV40 (COS-7 cells), according to the protocol supplied by the manufacturer of the transfection reagent (Lipofectamine, manufactured by Life Technologies, Inc.) of COS 7 cells.

Transfections were done in duplicate, i.e. two plates per construct.
1. In a 35 mm tissue culture plate, ~$2\times10^5$ cells were seeded in 2 ml D-MEM (Dulbecco's Modified Eagle Medium) containing 10% FBS (Fetal Bovine Serum) and nonessential amino acids (obtained from the ATCC, or from Life Technologies).
2. The cells were incubated at 37° C. in a $CO_2$ incubator until the cells were 70–80% confluent. This took 18–24 hours.
3. The following solutions were prepared in 12×75 mm sterile tubes: Solution A: For each transfection, 2 μg DNA (plasmid) diluted in 375 μl serum-free D-MEM (containing nonessential amino acids). Solution B: For each transfection, 6 μl LIPOFECTAMINE Reagent was diluted in 375 μl serum-free D-MEM.
4. The two solutions were combined, mixed gently, and incubated at room temperature for 30 min.
5. The cells were washed once with 2 ml serum-free D-MEM.
6. For each transfection, 750 μl serum-free D-MEM was added to each tube containing the lipid-DNA complexes. After gentle mixing, the diluted complex solution was added onto the washed cells.
7. The cells were incubated for 5 h at 37° C. in a $CO_2$ incubator.
8. 1.5 ml D-MEM with 20% FBS was added without removing the transfection mixture.
9. The medium was replaced at 18–24 h following start of transfection.

Cells were harvested at 2 and 4 days post-transfection. Cells were scraped from the plates and pelleted by centrifugation in 1.5 ml microcentrifuge tubes. Pellets from the duplicate transfection experiments were pooled. We isolated total nucleic acids from these cells, at two and four days post-transfection using the QIAamp DNA Mini Kit, according to the manufacturer's instructions (Qiagen). Two and a half micrograms of total nucleic acids from each sample was digested with 20 units of DpnI which cuts only dam-methylated DNA, i.e. the input plasmid DNA, at sequence GA*TC, where the A* is methylated (Sambrook et al., 1989). The restricted DNA was run on a 1% TAE agarose gel, stained with ethidium bromide. The DNA was transferred to a nylon membrane (Roche Molecular Biochemicals) by the standard alkaline capillary transfer Southern blot protocol (Sambrook et al., 1989). The RCR replicon DNAs were detected by Southern hybridization with a probe made from Construct 1, nonradioactively labeled with Digoxygenin by the random priming method, according to the protocol supplied by the manufacturer (Roche Molecular Biochemicals).

Figure 4:
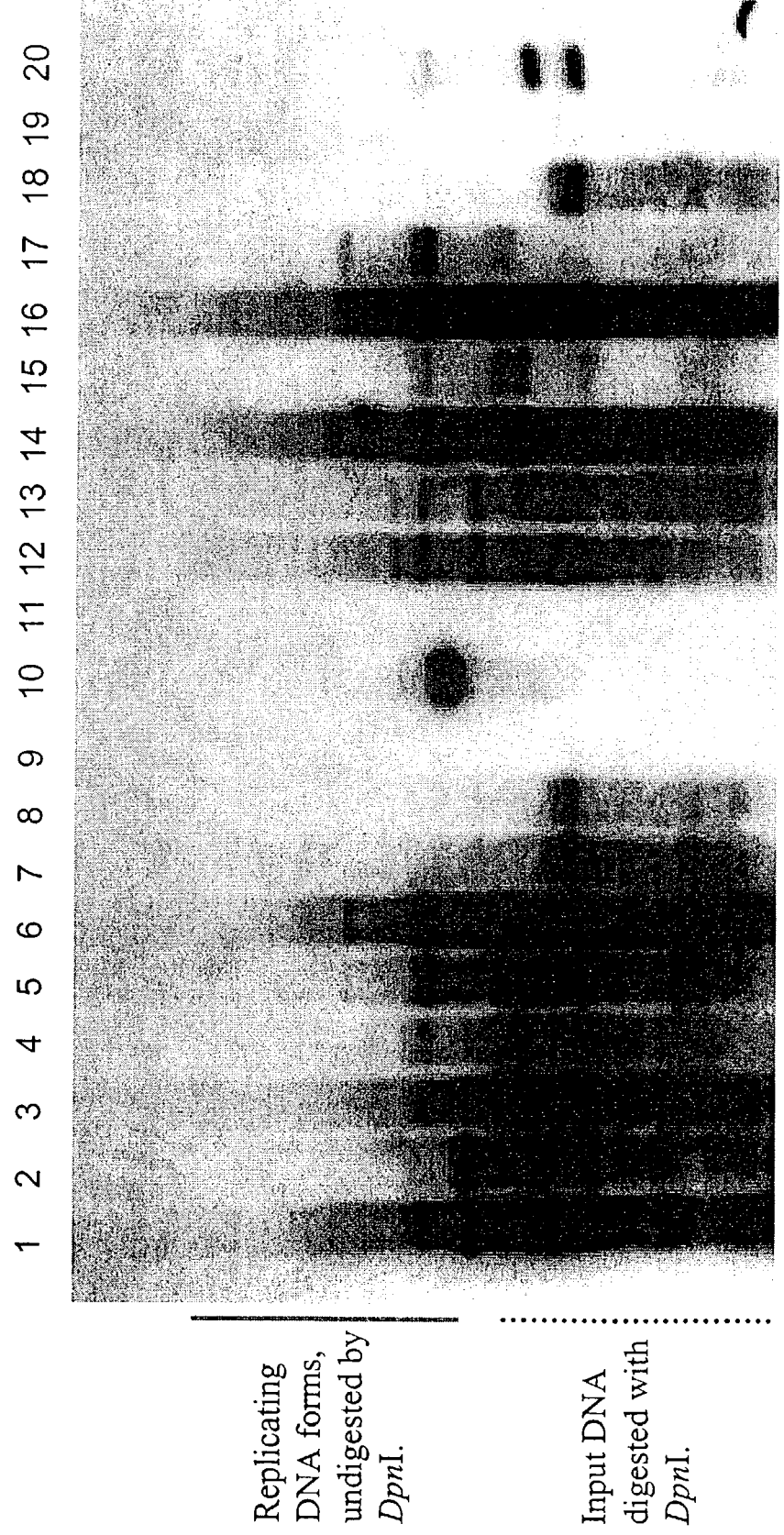
FIG. 4 shows a Southern blot of DNA isolated from cells transfected with PCV-containing constructs and control DNAs. Two and a half micrograms of total DNA from transfected cells was digested with an excess of DpnI restriction enzyme and electrophoresed in a 1.0% TAE agarose gel and stained with ethidium bromide. DNA was transferred to a nylon membrane by capillary transfer. The Southern blot was hybridized with a probe prepared from construct 1, which has homology with all input plasmid DNAs. Lanes 1 to 9 contain DNA isolated from COS-7 cells transfected with the following plasmids: Lane 1 & 2; Construct 1, DNA isolated at day 2 and day 4 post-transfection; Lanes 3&4: Construct 2, day 2 & 4; Lanes 5 & 6; construct 4, day 2 & day 4; Lanes 7 & 8;construct 6, day 2 & 4. Lanes 9 & 11 contain DNA isolated from untransfected cells; lane 10 contained a DNA molecular weight marker. Lanes 12 to 19 contain DNA isolated from CHO-K1 cells transfected with the following plasmids: lanes 12 & 13; Construct 7, day 2 & day 4. lanes 14 & 15: construct 2, day 2 & 4; lanes 16 & 17: construct 4, days 2 & 4 and lanes 18 & 19; construct 6, days 2 & 4. Lane 20 contains DNA isolated from PCV-positive cell line PK-15, used as a positive control for DNA hybridization. The hybridizing bands run at a significantly lower position, due to the virus's small size (1.8-kb) relative to the plasmid DNAs (greater than 4.0-kb).

FIG. 5 shows the results of the Southern Hybridization experiment. The probe DNA contains sequences (the ColE1 origin of replication) in common with all of the input plasmids, and should therefore hybridize with all replicating, and input plasmid DNAs. Digested, low molecular weight Dpn I-digested fragments of the input DNAs may be visible (less than 1.0-kb, indicated in FIG. 4); all replicating DNAs will remain undigested. All plasmids with SV40 ori sequences (constructs 2, 4, and 6) replicated in the COS-7 cells, as expected. Construct 1 (lanes 1 and 2) also appeared to be replicating in the COS-7 cells, indicating that the PCV RCR replicon was functioning, and replicating the linked non-viral DNA sequences. This shows that the PCV-derived RCR replicon can replicate in African Green Monkey kidney cells.

Constructs 2, 4, 6 and 7 were transfected into Chinese Hamster Ovary (CHO) cells. Cells transfected with constructs 6 and 7 exhibited green fluorescence, indicating expression of the GFP fusion protein. Total DNA was isolated from these cells at 2 and 4 days post-transfection. Southern blot analysis showed that constructs 2, 4 and 7, which contain PCV Rep and origin of replication sequences were all replicating in the transfected cells, whereas construct 6, an SV40 replicon, was not replicating. This shows that PCV RCR replicons can replicate, and express genes linked to the replicon, in Chinese Hamster Ovary (CHO) cells.

Constructs 1, 6 and 7 were transfected into COS-7 cells. The transfections were performed according to the methods suggested by the manufacturer of the transfection reagent (Effectene, from Qiagen). We used 1 μg of DNA, 8 μl of enhancer and 25 μl of Effectene per transfection.

Analysis

At one day post-transfection, cells transfected with construct 7 (PCV RCR plasmid) were clearly expressing the GFP-zeocin fusion gene, but cells transfected with construct 6 (with functional SV40 origin of replication sequences) were not. Thus, the PCV replicon expresses linked genes at a higher level, earlier than the cognate SV40 replicon. Constructs 1, 6 and 7 were also transfected into CHO cells, with similar results one day post-transfection.

In another experiment to evaluate GFP gene expression after transfection of CHO-K1 cells, we compared timing and relative intensity of GFP fluorescence after transfection of cells with constructs 6 (non-replicating, with no PCV sequences) and 7 (a PCV-derived construct). Cells were transfected in parallel by two different methods: with Effectene (Qiagen) and with a standard calcium phosphate precipitation protocol.

Effectene Transfection Method

For the effectene transfection method, one microgram of plasmid DNA was mixed with DNA condensation buffer (Buffer EC), to a total volume of 150 μl. Eight microlitres of Enhancer were added, and the DNA solution was mixed by vortexing for one second. The DNA mixture was incubated at room temperature for 5 minutes. Effectene transfection reagent (25 μl) was added to the DNA-enhancer mixture, and mixed by pipetting up and down five times. The samples were incubated at room temperature to allow complex formation.

While complex formation was occurring, the growth medium was gently aspirated from the plates, and the cells were washed once with phosphate buffered saline (PBS). Four milliliters of fresh growth medium was then added to the cells.

One milliliter of growth medium was added to the reaction tube containing the transfection complexes; the solution was then mixed and immediately added drop-wise onto the cells in 60-mm dishes. The dish was gently swirled to ensure uniform distribution of the complexes. The cells with transfection complexes were incubated at 37° C. and 5% $CO_2$ to allow for gene expression.

The expression of GFP in transfected cells was observed at three and seven days post-transfection. The results from observation of cells transfected by the Effectene method are tabulated below (Table 1/LSB #3).

Construct 3: non-replicating plasmid DNA, no GFP gene (DNA control)

Construct 6: non-replicating plasmid DNA, GFP-zeocin fusion gene, should express GFP in transfected cells.

Construct 7: plasmid DNA with PCV replicon and the same GFP-zeocin fusion gene as construct 6: May be capable of replication.

| Dish # | Construct | Day 3 Observations | Day 7 Observations |
|---|---|---|---|
| 1 | 3 | No GFP, cells look healthy | No GFP, cells growing well |
| 2 | 6 | 4 to 5% GFP + ve, low level expression | Small number of GFP + ve cells |
| 3 | 7 | 10% GFP + ve, low to moderate expression | Very many GFP + ve cells, both dim and bright |
| 5 | No DNA | No GFP; cells growing well | No GFP |

REFERENCES

Ach R A, Durfee T, Miller A B, Taranto P, Hanley-Bowdoin L, Zambryski P C, Gruissem W (1997) RRB1 and RRB2 encode maize retinoblastoma-related proteins that interact with a plant-D-type cyclin and geminivirus replication proteins. *Molecular and Cellular Biology* 17: 5977–86.

Abouzid A M, Frischmuth T, Jeske H (1988) A putative replicative form of abutilon mosaic virus (gemini group) in a chromatin-like structure. *Mol. Gen. Genet.* 212: 252–258

Bassami M R, Berryman D, Wilcox G E, Raidal S R (1998) Psitticine beak and feather disease virus nucleotide sequence and analysis and its relationship to porcine Circoviruses, plant Circoviruses and chicken anaemia virus. *Virology* 249: 453–459.

Boevink P, Chu P W and Keese P (1995) Sequence of subterranean clover stunt virus DNA: affinities with the Geminiviruses. *Virology* 207: 354–361.

Burns T M, Harding R M, Dale J L (1995) The genome organization of banana bunch top virus: analysis of six ssDNA components. *J Gen. Virol.* 76: 1471–1482

Castellano M M, Sanz-Burgos A P, Gutierrez C (1999) Initiation of DNA replication in a eukaryotic rolling-circle replicon: identification of multiple DNA-protein complexes at the geminivirus origin. *J Mol. Biol.* 290: 639–652.

Elmer J S, Brand L, Sunter G, Gardiner W E, Bisaro D M, Rogers S G (1988) Genetic analysis of the tomato golden mosaic virus. II. The product of the AL1 coding sequence is required for replication. *Nucl. Acids Res.* 16: 7043–7060.

Frischmuth T, Stanley J (1998) Recombination between viral DNA and transgenic coat protein gene of African cassava mosaic virus. *Journal of General Virology* 79: 1265–71.

Gibbs M J, Weiller G F (1 999) Evidence that a plant virus switched hosts to infect a vertebrate and then recombined with a vertebrate-infecting virus. *Proc. Natl. Acad. Sci. USA* 96: 8022–8027

Grafi G et al. (1996) A maize cDNA encoding a member of the retinoblastoma protein family: involvement in endoreduplication. *Proc. Natl. Acad. Sci. USA* 93: 8962–8967.

Hafner G J, Stafford M R, Wolter L C, Harding R M, Dale J L (1997) Nicking and joining activity of banana bunchy top virus replication protein in vitro. *J. Gen. Virol.* 78: 1795–1799

Hanley-Bowdoin L, Settlage S B, Orozco B M, Nagar S, Robertson D (1999) Geminiviruses: models for plant DNA replication, transcription, and cell cycle regulation. *Critical Reviews in Plant Sciences* 18: 71–106.

Hayes R J et al. (1988) Gene amplification and expression in plants by a replicating geminivirus vector. *Nature* 334: 179–182.

Ilyina T V, Koonin E V (1992) Conserved sequence motifs in the initiator proteins for rolling circle replication encoded by diverse replicons from eubacteria, eucaryotes and archaebacteria. *Nucl. Acids Res.* 20: 3279–3285

Katul L, Timchenko T., Gronenborn B, Vetten H J (1998) Ten distinct circular ssDNA components, four of which encode putative replication-associated proteins, are associated with the faba bean necrotic yellows virus genome. *J. Gen. Virol.* 79: 3101–3109.

Lazarowitz S G (1999) Probing plant cell structure and function with viral movement proteins. *Current Opinion in Plant Biology* 2: 332–338.

Mankertz A, Mankertz J, Wolf K, Buhk H-J (1998) Identification of a protein essential for replication of porcine Circovirus. *J. Gen. Virol.* 79: 381–384.

Mankertz A, Persson F, Mankertz J, Blasess G, Buhk H-J (1997) Mapping and characterization of the origin of DNA replication of porcine Circovirus. *J. Virol.* 71: 2562–2566

Mankertz J, Buhk H-J, Blaess G, Mankertz A (1998) Transcription analysis of porcine Circovirus (PCV). *Virus Genes* 16: 267–276

Mansoor S, Kahn S H, Bashir A, Saeed M, Zafar Y, Malik K A, Briddon R, Stanley J, Markham P G (1999) Identification of a novel circular single-stranded DNA associated with cotton leaf curl disease in Pakistan. *Virology* 259: 190–199

Meehan B M, Creelan J L, McNulty M S, Todd D (1997) Sequence of porcine Circovirus DNA: affinities with plant Circoviruses. *J. Gen. Virol.* 78: 221–227

Meehan B M, McNeilly F, Todd D, Kennedy S, Jewhurst V A, Ellis J A, Hassard L E, Clark E G, Haines D M, Allan G M (1998) Characterization of novel Circoviruses associated with wasting syndromes of pigs. *J. Gen. Virol.* 79: 2171–2179

Morozov I, Sirinarumitr T, Sorden S D, Halbur P G, Morgan M K, Yoon K-J, Paul P S (1998) Detection of a novel strain of porcine Circovirus in pigs with postweaning multisystemic wasting syndrome. *J. Clin. Microbiol.* 36: 2535–2541.

Mushahwar I K, Erker J C, Muerhoff A S, Leary T P, Simons J N, Birkenmeyer L G, Chalmers M L, Pilot-Matias T J, Dexai S M (1999) Molecular and biophysical characterization of TT virus: evidence for a new virus family infecting humans. *Proc. Natl. Acad. Sci. USA* 96: 3177–3182

Nagar S et al. (1995) A geminivirus induces expression of a host DNA synthesis protein in terminally differentiated plant cells. *Plant Cell* 7: 705–719.

Palmer K E, Rybicki E P (1997) The use of Geminiviruses in biotechnology and plant molecular biology, with particular focus on Mastreviruses. *Plant Science* 129: 115–130

Palmer K E, Rybicki E P (1998) The molecular biology of Mastreviruses. *Adv. Virus Research* 50: 183–234

Pringle C R (1999) Virus taxonomy-1999. The universal system of virus taxonomy, updated to include the new proposals ratified by the International Committee on Taxonomy of Viruses during 1998. *Arch Virol.* 144: 421–429

Saunders K, Stanley J (1999) A Nanovirus-like DNA component associated with yellow vein disease of Ageratum conyzoides: evidence for interfamilial recombination between plant viruses. *Virology* 264: 142–152.

Timmermans M C P, Das O P, Messing J (1994) Geminiviruses and their uses as extrachromosomal replicons. *Annu. Rev. Plant Physiol. Plant Mol. Biol.* 45: 79–112.

van Regenmortel M H V, C. M. Fauquet, D. H. L. Bishop, E. B. Carsten, M. K. Estes, S. M. Lemon, J. Maniloff, M. A. Mayo, D. J. McGeoch, C. R. Pringle, R. B. Wickner (1999) Virus Taxonomy: Seventh Report of the International Committee on Taxonomy of Viruses. Springer Verlag: Wien.

Ward A et al. (1988) Expression of a bacterial gene in plants mediated by infectious geminivirus DNA. *EMBO Journal* 7:1583–1587.

Xie Q et al. (1995) Identification and analysis of a retinoblastoma binding motif of the replication protein of a plant DNA virus: requirement for efficient viral replication. *EMBO Journal* 14: 4073–4082.

Xie Q et al. (1996) Plant cells contain a novel member of the retinoblastoma family of plant growth regulatory proteins. *EMBO J.* 15: 4900–4968.

Xie Q, Sanz-Burgos A P, Guo H, Garcia J A, Gutierrez C (1999) GRAB proteins, novel members of the NAC domain family, isolated by their interaction with a geminivirus protein. *Plant Mol. Biol.* 39: 647–656.

Although the invention has been described with reference to the presently preferred embodiments, it should be understood that various modifications could be made without departing from the spirit of the invention.

What is claimed is:

1. A rolling circle DNA replicon capable of rolling circle replication in a host eukaryotic cell, comprising the following elements, present on the same DNA molecule:
   a) a Rep gene open reading frame from a virus belonging to viral taxonomic families Geminiviridae, Circoviridae or genus Nanovirus, wherein said Rep gene open reading frame is placed under transcriptional control of a promoter, and wherein said promoter is placed 5' of the gene;
   b) sequences that are required to be present in cis on the rolling circle DNA replicon in order that a Rep protein might promote replication of the rolling circle DNA replicon;
   c) an expression cassette for expression of an ancillary protein that is capable of creating a cellular environment allowing for replication of the rolling circle DNA replicon in the host eukaryotic cell wherein said ancillary protein is a viral protein; and
   d) at least one expression cassette comprising an RNA polymerase II promoter, a multiple cloning site, and transcription termination and polyadenylation signals suitable for transcription of RNA molecules not normally intrinsic to a Geminiviral, Circoviral or Nanoviral genome.

2. The rolling circle DNA replicon according to claim 1, wherein at least one promoter is chosen to be one that can function in a host eukaryotic cell type of interest.

3. The rolling circle DNA replicon according to claim 1, wherein at least one promoter has tissue or cell-type specificity.

4. The rolling circle DNA replicon according to claim 1, wherein at least one promoter is an inducible promoter subject to chemical or other environmental induction.

5. The rolling circle DNA replicon according to claim 1, wherein said sequences that are required to be present in cis on the rolling circle DNA replicon in order that the Rep protein might promote replication of the rolling circle DNA replicon are obtained from the group consisting of Nanoviruses, Circoviruses, begomoviruses and curtoviruses.

6. The rolling circle DNA replicon according to claim 1, wherein said sequences that are required to be present in cis on the rolling circle DNA replicon in order that the Rep protein might promote replication of the rolling circle DNA replicon are:
   a) the viral origin of replication that contains the conserved stem-loop structure,
   b) TANTATTAC nanonucleotide sequence; and
   c) flanking intergenic sequences, wherein said flanking intergenic sequences comprise at least 90 bases 5' to the start of the conserved stem-loop structure and 10 to 100 bases 3' of the end of the conserved stem-loop structure.

7. The rolling circle DNA replicon according to claim 1, wherein said sequences that are required to be present in cis on the rolling circle DNA replicon in order that the Rep protein might promote replication of the rolling circle DNA replicon are long intergenic regions and short intergenic regions obtained from a mastrevirus.

8. The rolling circle DNA replicon according to claim 1, wherein a second viral ancillary protein is expressed.

9. A method of making a rolling circle DNA replicon which replicates in a host eukaryotic cell, comprising combining:
   a) a Rep gene open reading frame from a virus belonging to the viral taxonomic families Geminiviridae, Circoviridae or genus Nanovirus, said Rep gene open reading frame is placed under transcriptional control of a promoter, wherein said promoter is placed 5' of the gene;
   b) (i) an origin of replication of the same virus of the Rep gene open reading frame, (ii) a TANTATTAC sequence, and (iii) a stem-loop structure flanking sequence present in cis on the rolling circle DNA replicon in order for the Rep protein to promote replication of the rolling circle DNA replicon;
   c) an expression cassette for expression of an ancillary protein capable of creating a cellular environment allowing for replication of the rolling circle DNA replicon in the host eukaryotic cell wherein said ancillary protein is a viral protein; and
   d) at least one expression cassette with an RNA polymerase II promoter, a multiple cloning site, and transcription termination and polyadenylation signals suitable for transcription of RNA molecules not normally intrinsic to a geminiviral, circoviral or nanoviral genome.

10. The replicon of claim 1, wherein the ancillary protein comprises a replication-associated early gene product of a Geminiviridae, Circoviridae or Nanovirus virus.

11. The replicon of claim 1, wherein the ancillary protein comprises a redundant Rep gene ORF from a virus belonging to a Geminiviridae, Circoviridae or Nanovirus virus.

12. The method of claim 9, wherein the ancillary protein comprises a replication-associated early gene product of a Geminiviridae, Circoviridae or Nanovirus virus.

13. The method of claim 9, wherein the ancillary protein comprises a redundant Rep gene ORF from a virus belonging to a Geminiviridae, Circoviridae or Nanovirus virus.

* * * * *